United States Patent

Briving et al.

[11] Patent Number: 5,439,917
[45] Date of Patent: Aug. 8, 1995

[54] ACTIVE COMPOUNDS

[75] Inventors: Carin Briving, Billdal; Stig Carlsson, Mölnlycke; Robert Carter, Mölnlycke; Marie Elebring, Mölnlycke; Thomas Kühler, Göteborg; Peter Nordberg, Göteborg; Ingemar Starke, Göteborg; Arne Svensson, Mölndal, all of Sweden

[73] Assignee: Aktiebolaget Astra, Sodertalje, Sweden

[21] Appl. No.: 122,442

[22] PCT Filed: Mar. 25, 1992

[86] PCT No.: PCT/SE92/00190
§ 371 Date: Sep. 27, 1993
§ 102(e) Date: Sep. 27, 1993

[87] PCT Pub. No.: WO92/17477
PCT Pub. Date: Oct. 15, 1992

[30] Foreign Application Priority Data

Mar. 27, 1991 [SE] Sweden .................... 9100920

[51] Int. Cl.⁶ .................... A61K 31/435; C07D 471/04
[52] U.S. Cl. .................... 514/300; 546/113
[58] Field of Search .................... 546/113; 514/300

[56] References Cited

PUBLICATIONS

Saify, Pakistan J. Pharmacology, vol. 2(2), pp. 43–46 (1985).

Primary Examiner—Bernard Dentz
Attorney, Agent, or Firm—White & Case

[57] ABSTRACT

Therapeutically active compounds of the formula:

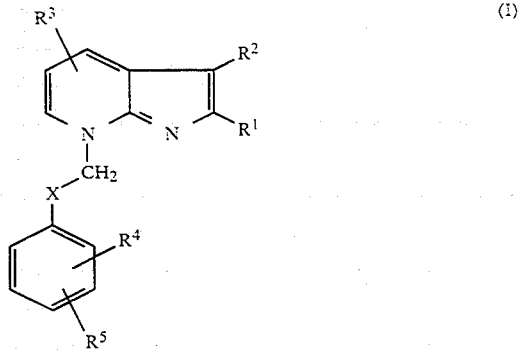

wherein the variables are defined in the specification are provided.

33 Claims, No Drawings

ACTIVE COMPOUNDS

This application is a 371 of PCT/SE92/00190.

FIELD OF THE INVENTION

The object of the present invention is to provide novel compounds, and therapeutically acceptable salts thereof, which inhibit exogenously or endogenously stimulated gastric acid secretion and thus can be used in the prevention and treatment of peptic ulcer.

The present invention also relates to the use of the compounds of the invention for inhibiting gastric acid secretion in mammals including man. In a more general sense, the compounds of the invention may be used for prevention and treatment of gastrointestinal inflammatory diseases, and gastric acid-related diseases in mammals including man, such as gastritis, gastric ulcer, duodenal ulcer, reflux esophagitis and Zollinger-Ellison syndrom. Furthermore, the compounds may be used for treatment of other gastrointestinal disorders where gastric antisecretory effect is desirable e.g. in patients with gastrinomas, and in patients with acute upper gastrointestinal bleeding. They may also be used in patients in intensive care situations, and pre- and postoperatively to prevent acid aspiration and stress ulceration. The invention also relates to pharmaceutical compositions containing at least one compound of the invention, or a therapeutically acceptable salt thereof, as active ingredient. In a further aspect, the invention relates to processes for preparation of such new compounds, and to the use of the active compounds for the preparation of pharmaceutical compositions for the medical use indicated above.

PRIOR ART

Certain pyrrolo[2,3-b]pyridines have been disclosed in Sally Pak.J. Pharmacol. 86 Vol 2(2) pp 43–36 (1985), Saify, J. Pharm. Univ. Kar. 2(2):99–103 (1984), TimPe et al. J. Prakt. Chem. 80 Vol 322(3) pp 517–21 (1980) Ogali et al., Indian Journal of Chemistry Vol. 27B, 656–651 (1988).

THE INVENTION

It has been found that compounds of the following formula I are effective as inhibitors of gastric acid secretion. The compounds of the formula I exert this effect by inhibiting the gastrointestinal $H^+K^+$-ATPase enzyme.

The compounds of the invention are of the following formula I:

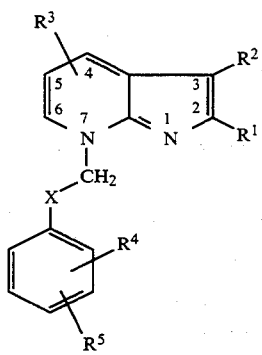

I or a pharmaceutically acceptable salt thereof, wherein X represents

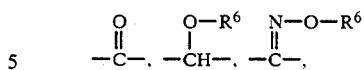

or $-CH_2-$;

$R^1$ represents H, lower alkyl, $CH_2-O-R^7$ halogen phenyl or phenyl substituted with (1-6c) alkyl, (1-6c) alkoxy, (1-6c) acyl, halogen, $CF_3$, CN, $NH_2$, $NO_2$ or (1-6c) alkoxycarbonyl;

$R^2$ represents H, lower alkyl, $CH_2CN$,

halogen,
$O-R^8$,

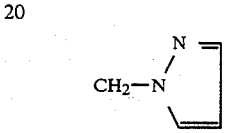

S—CN, $CH_2OH$, $CH_2C\equiv CH$, $CF_3,CH_2NC$ or $NH_2$;
$R^3$ represents H, lower alkyl, $CF_3$, $O-R^9$, $NH_2$, lower alkylamino, di-lower alkylamino, halogen, CN,

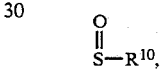

S—$R^{10}$ or NHCOR$^{10}$;
$R^4$ and $R^5$ which are the same or different represent H lower alkyl, CN, halogen, $O-R^{11}$, $NO_2$, $NH_2$, lower alkylamino, di-lower alkylamino, S—$R^{12}$, NHCOR$^{13}$,

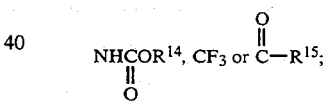

$R^6$, $R^7$, $R^8$, $R^9$, $R^{11}$, and $R^{13}$ which are the same or different, represent H or lower alkyl;
$R^{10}$ represents lower alkyl or phenyl lower alkyl;
$R^{12}$ and $R^{14}$ which are the same or different represent lower alkyl;
$R^{15}$ represents H, lower alkyl, OH or lower alkoxy; provided that $R^1$ and $R^2$ are not simultaneously H. As used herein, the term "lower" when applied to hydrocarbon groups, alkoxy-, alkylamino-, dialkylamino-, alkylthio, alkylsulfinyl-, phenylalkylthio-, phenylalkylsulfinyl, acylamino- or alkoxycarbonyl groups includes straight and branched chain hydrocarbon group having up to 6 carbon atom.

The term halogen includes fluoro, chloro bromo and iodo.

Both the pure enantiomers, racemic mixtures and unequal mixtures of two enantiomers are within the scope of the present invention. It should be understood that all the diastereomeric forms possible (pure enantiomers or racemic mixtures) are within the scope of the invention. Also included in the invention are derivatives of the compounds of the formula I which have the biological function of the compounds of the formula I.

Depending on the process conditions and the starting materials, the end products of the formula I are obtained either in neutral or salt form. Both the free base or acid and the salts of these end products are within the scope of the invention.

Acid addition salts of the new compounds may in a manner known per se be transformed into free base using basic agents such as alkali or by ion exchange. The free base obtained may also form salts with organic or inorganic acids. In the preparation of acid addition salts, preferably such acids are used which form suitably therapeutically acceptable salts.

Examples of such acids are hydrohalogen acids, sulfonic acids, phosphoric acid, nitric acid, aliphatic, alicyclic, aromatic or heterocyclic carboxyl or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulfonic acid, ethanesulfonic acid, hydroxyethanesulfonic acid, ethylenesulfonic acid, halogenbensenesulfonic acid, toluenesulfonic acid or naphtylsulfonic acid.

These or other salts of the new pyrrolo[2,3-b]pyridine, as e.g. picrates, may serve as purifying agents of the free bases obtained. Salts of the bases may be formed, separated from solution, and then the free base can be recovered in higher purity from a new salt solution.

Base addition salts of the new compounds may be transformed into the acid form using inorganic or organic acids, and then reconverted to a therapeutically suitable salt such as sodium and potassium salts by addition of NaOH and KOH, respectively.

Preferred groups of compounds of the formula I are:
1. Compounds wherein X is

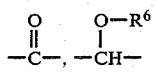

or —CH$_2$— and R$^6$ is as defined above

2. Compounds wherein R$^1$ is lower alkyl, optionally substituted phenyl, CH$_2$OR$^7$ or halogen and R$^7$ is as defined above.

3. Compounds wherein R$^2$ is H, lower alkyl, CH$_2$C≡CH, CH$_2$OH, CH$_2$CN,

CH2NC, NH$_2$,

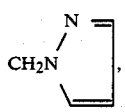

SCN, halogen or CF$_3$.

4. Compounds wherein R$^3$ is H, lower alkyl, O—R$^9$, NH$_2$, lower alkylamino, di-lower alkylamino, C≡N, S—R$^{10}$,

halogen, CF$_3$ or NHCOR$^{10}$ and R$^9$ and R$^{10}$ are as defined above.

5. Compounds wherein R$^4$ and R$^5$ are the same or different and selected from H, lower alkyl, C≡N, halogen, O—R$^{11}$, NO$_2$, NH$_2$, lower alkylamino, di-lower alkylamino, S—R$^{12}$,
NHCOR$^{13}$, CF$_3$ or

and R$^{11}$, R$^{12}$, R$^{13}$ and R$^{15}$ are as defined above.

More preferred groups of compounds of the formula I are:
1. Compounds wherein X is

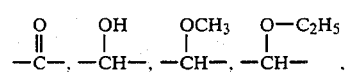

or —CH$_2$—

2. Compounds wherein R$^1$ is CH$_3$, C$_2$H$_5$, CH(CH$_3$)$_2$, CH$_2$CH$_2$CH$_3$, Cl, Br or phenyl 3. Compounds wherein R$^2$ is H, CH$_3$, C$_2$H$_5$, CH$_2$CN,

F, Cl, Br, SCN, CH$_2$OH, CH$_2$C≡NCH, CF$_3$ or CH$_2$NC

4. Compounds wherein R$^3$ is H, CH$_3$, C$_2$H$_5$, CH(CH$_3$)$_2$, CH$_2$CH$_2$CH$_3$, CF$_3$, OH, OCH$_3$, OC$_2$H$_5$, OCH(CH$_3$)$_2$, NH$_2$, NHCH$_3$, NHC$_2$H$_5$, N(CH$_3$)$_2$, N(C$_2$H$_5$)$_2$, F, Cl, Br, S—CH$_3$, S—C$_2$H$_5$,

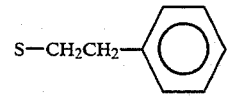

or NHCOCH$_3$.

5. Compounds wherein R$^4$ and R$^5$ are the same or different and selected from H, CH$_3$, C$_2$H$_5$, CH(CH$_3$)$_2$, F, Cl, Br, OH, OCH$_3$, OC$_2$H$_5$, OCH(CH$_3$)$_2$, NO$_2$, NH$_2$, NHCH$_3$, NHC$_2$H$_5$, N(CH$_3$)$_2$, N(C$_2$H$_5$)$_2$, S—CH$_3$ or CF$_3$.

The radical R$^3$ is in position 4, 5 or 6, preferably in position 5 or 6 in the compound of Formula I.

The radicals R$^4$ and R$^5$ are in positions 2, 3, 4, 5 or 6 of the phenyl nucleus.

The most preferred compound of the invention is:

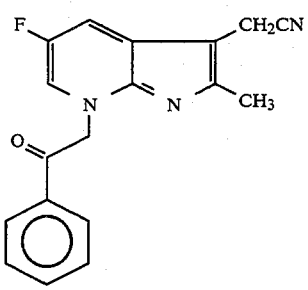

Other preferred compounds of the invention are:

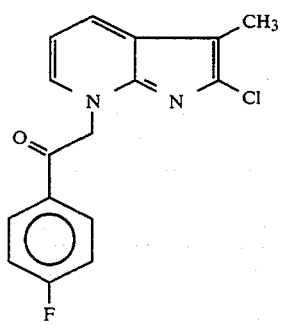
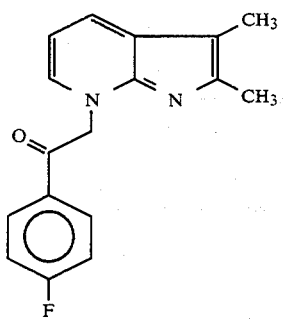
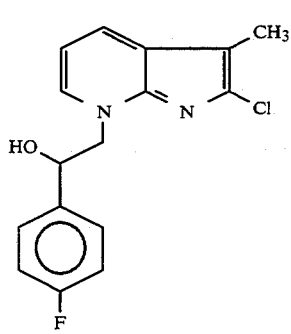
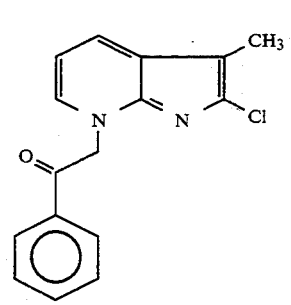
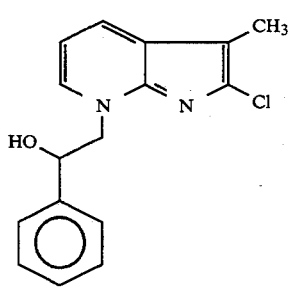
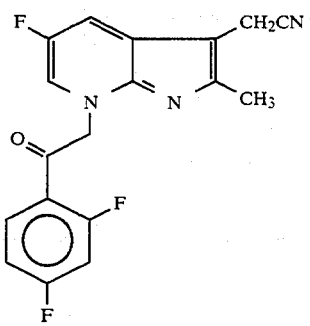
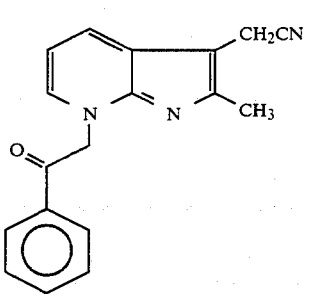
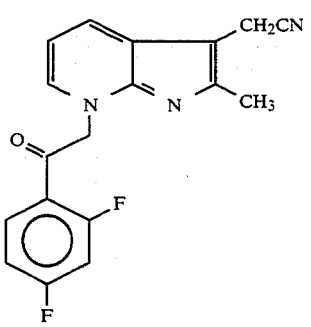
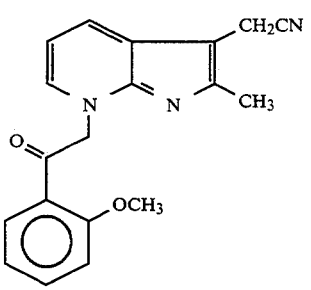
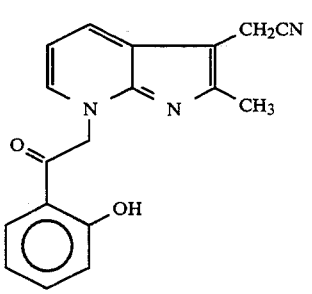

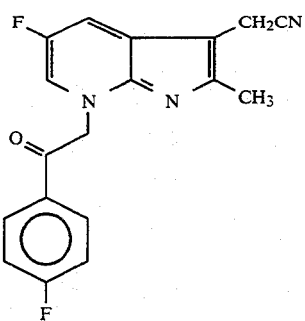

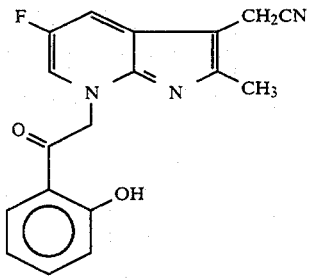

PREPARATION

The present invention also provides processes for the manufacture of the compounds with the general formula I. The compounds may be prepared in the following way.

A. A compound of the general formula II

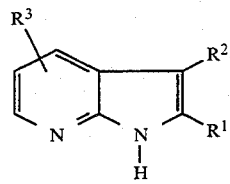

wherein $R^1$, $R^2$ and $R^3$ are as defined above is reacted with a compound of the general formula III

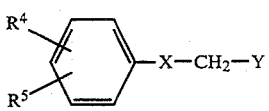

wherein X, $R^4$ and $R^5$ are as defined above and Y is a leaving group, such as a halide, tosyloxy or mesyloxy whereby a compound of the general formula I, wherein X, $R^1$, $R^2$, $R^3$, $R^4$ and $R^5$ are as defined above is obtained. It is convenient to conduct this reaction in a solvent. The solvent used for the reaction is preferably a polar solvent such as acetonitril or dimethyl formamide or an alcohol, e.g. ethanol or isopropanol.

The reaction temperature ranges usually from about 20° C. to about the boiling point of the solvent used, more preferably from about 20° C. to about 80° C. The reaction time ranges from about 0.1 to about 96 hours.

B. Compounds of the formula I wherein X is CHOH and $R^1$, $R_2$, $R^3$, $R^4$ and $R^5$ are as defined above are prepared by reducing a compound of formula I wherein X is C=O and $R^1$, $R^2$, $R^3$, $R^4$ and $R^5$ are as defined above, e.g. by reacting with a reducing agent such as NaBH$_4$, LiAlH$_4$ or by catalytic hydrogenation.

C. Compounds of the formula I wherein $R^2$ is OH and X, $R^1$, $R^3$, $R^4R^5$ are as defined above are prepared by reacting a compound of formula I wherein X, $R^1$, $R^3$, $R^4$ and $R^5$ are as defined above and $R^2$ is O(1–6C)alkyl with a dealkylation agent such as B(Br)$_3$ or (CH$_3$)$_3$SiI.

D. Compounds of the formula I wherein X is CHO—$R^6$ and $R^1$, $R^2$, $R^3$, $R^4$ and $R^5$ are as defined above are prepared by reacting a compound of formula I wherein X is CHOH and $R^1$, $R^2$, $R^3$, $R^4$ and $R^5$ are as defined above with a compound of formula IV $$R^6-Z \qquad\qquad IV$$

wherein $R^6$ is as defined above and Z is a reactive esterified hydroxy group.

E. Compounds of the formula I wherein $R^4$ is 2—OH, $R^5$ is different from $R^4$, and X $R^1$, $R^2$ and $R^3$ are as defined above are prepared by reacting a compound of formula I wherein X, $R^1$, $R^2$, $R^3$ and $R^5$ are as defined above provided that $R^5$ is different from $R^4$, and $R^4$ is 2—O($C_1$-$C_6$alkyl) with a dealkylation agent such as $B(Br)_3$ or $(CH_3)_3SiI$.

The compound of the formula I thus obtained is then, if desired, converted to a pharmaceutically acceptable salt.

EXAMPLES

Example 1

Preparation of 2-methyl -7- (2-phenylethyl)-pyrrolo[2,3-b]pyridine

A solution of 85 mg (0.64 mmol) of 2-methyl-pyrrolo[2,3-b]pyridine and 140 mg( 0.76 mmol) of (2-bromoethyl)benzene in 1 ml acetonitrile was refluxed for 40 h. The solvent was evaporated and the residue was treated with ether. The solid that formed was isolated by filtration to give 188 mg (62%) of 2-methyl-7-(2-phenylethyl)pyrrolo[2,3-b]pyridinehydrobromide.

($^1$H-NMR, 500 MHz, CDCl$_3$) 2.78(s,3H), 3.44 (t, 2H), 5.40(t,2H) 6.44(s,1H), 6.97(dd,2H) , 7.08(dd, 1H) , 7.18(m, 3H), 7.31(d, 1H) , 8.17(d, 1H) .

Example 2

3-Chloro-2-methyl-7-(2-phenylethyl)pyrrolo[2,3-b[pyridine hydrobromide

A solution of 28.4 mg (0.17 mmol) of 3-chloro-2-methyl pyrrolo [2,3-b]pyridine and 36 mg (0.2mmol) of (2bromoethyl)benzene in 0.4 ml of dimethylformamid was heated at 80° C. for 20 h. The solvent was evaporated. The solid that formed was treated with ethyl acetate and isolated by filtration to give 30 mg (50%) of 3 -chloro-2-methyl-7-(2-phenylethyl)pyrrolo[2,3-b]pyridine hydrobromide.

($^1$H-NMR, 500 MHz,CDCl$_3$) 2.77(s,3H), 3.45(t,2H), 5.40(t,2H), 6.95(dd,2H), 7.14(dd, 1H) , 7.2(m, 3H), 7.28(d, 1H), 8.24 (d, 1H).

Example 3

3-Cyanomethyl-2-methyl-7-(2-phenylethyl)pyrrolo[2,3-b]pyridine

A solution of 130 mg (0.76 mmol) of 3-cyanomethyl-2-methyl-pyrrolo[2,3-b]pyridine and 150 mg (0.81 mmol) of 2-bromoethyl-benzene in 2 ml of acetonitrile was refluxed for 40 h. The solvent was evaporated and the crude product was chromatographed on silica gel with ethyl acetate: methanol: water 100:12:4. Recrystallization from a small amount of ether: petroleumether 1:1 gave 53 mg (25%) of 3-cyanomethyl-2-methyl-7-(2-phenylethyl)pyrrolo[2,3-b]pyridine.

($^1$H-NMR, 500 MHz, CDCl$_3$) 2.59 (s, 3H), 3.34(t,2H), 3.83(s,2H), 4.84(t,2H), 6.66(dd, 1H) , 7.01 (dd, 2H), 7.07(d, 1H) , 7.23(m, 3H) , 7.94(d, 1H).

Example 4

3 -Methyl-7-(2-phenylethyl)pyrrolo[2,3-b ]pyridine hydrobromide.

A solution of 0.3 g (2.3 mmol) 3-methylpyrrolo[2,3-b]pyridine and 0.5 g (2.7 mmol) (2-bromoethyl)benzene in 10 ml acetonitril was refluxed for 72 h. The solvent was evaporated and the solid that formed was treated with ether. Recrystalization from ethyl acetate gave 0.2 g (27%) of the title compound as a white solid.

($^1$H-NMR, 300 MHz, CDCl$_3$) 2.35(s,3H), 3.45(t,2H), 5.4(t,2H), 6.9–7.0(m, 2H), 7.1(t,1H), 7.2–7.3(m, 3H), 7.4(dd, 1H), 7.55(s,1H) , 8.25(dd, 1H) .

Example 5

2-Hydroxymethyl-3-methyl-7-(2-phenylethyl)pyrrolo[2,3-b]pyridine hydrobromide

A solution of 0.11 g (0.68 mmol) 2-hydroxymethyl-3-methylpyrrolo [2,3-b]pyridine and 0.13 g (7 mmol) (2-bromoethyl)benzene in 5 ml acetonitril was refluxed for 24 h. The solvent was evaporated. Chromatography on silica gel eluting with methylene chloride and methanol (10:1) gave the desired product. (0.03 g 13%).

($^1$H-NMR, 500 MHz,CDCl$_3$), 2.35(s,3H), 3.4(t,2H), 4.95(s,2H), 5.1(t,2H), 6.95–7.0(m, 2H), 7.05(t,1H), 7.2–7.25(m, 3H), 7.35(dd, 1H) , 8.15(dd, 2H) .

Example 6

2-Chloro-3-methyl-7-(2-phenylethyl)pyrrolo[2,3-b]pyridine

A solution of 0.1 g ( 0.6 mmol) 2-chloro-3-methylpyrrolo-[2,3-b]pyridine and 0.14 g (0.78 mmol) (2-bromoethyl)-benzene in 10 ml acetonitril was refluxed 72 h. The solvent was evaporated. The solid that formed was treated with ether and ethyl acetate and isolated by filtration. Chromatography on silica gel eluting with methylene chloride and methanol (10:1) gave the desired product. (0.03 g 18% ).

(1H-NMR, 300 MHz,CDCl$_3$) 2.3(s,3H), 3.35(t,2H), 4.8(t,2H), 6.65(t,1H), 6.95–7.0(m,2H), 7.05(dd, 1H), 7.2–7.25(m, 3H), 7.8(dd, 1H).

Example 7

6-Amino-2,3-dimethyl-7-(2-phenylethyl)-pyrrolo[2,3-b]pyridine hydrobromide

A solution of 6-amino-2,3 -dimethyl-pyrrolo [2,3-b]pyridine (1.0 g, 6,2 mmol ) and phenethyl bromide (1,7 g, 9,3 mmol ) in 30 ml CH$_3$CN was refluxed for 48 h. The mixture was allowed to cool and the precipitate was filtered off. Chromatography on silica gel eluting with methylene chloride and methanol (9:1) gave the desired product (0,1 g, 6%).

($^1$H-NMR, 500 MHz, CDCl$_3$+CD$_3$OD) 2,10(s,3H), 2,25(s,3H), 3,20(t,2H), 4,70(t,2H), 6,60 (d, 1H) , 7,10 (dd, 2H) , 7,15–7,20(m, 3H), 7,75(d, 1H).

Example 8

2,3 -Dimethyl-7-phenacylpyrrolo[2,3-b]pyridine.

A solution of 2,3-dimethylpyrrolo[2,3-b]pyridine (146 mg, 1 mmol) and phenacyl chloride (170 mg, 1.1 mmol) in 3 ml CH3CN was refluxed for 4.5 h. The mixture was allowed to cool and the precipitated product filtered off and washed with a small volume of ice cold CCl$_4$ affording 207 mg (69%) pure title compound as the hydrochloride salt.

($^1$H-NMR, 300 MHz, DMSO-d$_6$), 2.29(s,3H), 2.42(s,3H), 6.66(s,2H), 7.65(m,3H), 7.80(t,1H), 8.11(d,2H), 8.47(d, 1H), 8.62(d, 1H), 13.5(b, 1H).

Example 9

3-Chloro-2-methyl-7-phenacylpyrrolo[2,3-b]pyridinehydrochloride

A solution of 200 mg (1.2 mmol) of 3-chloro-2-methyl pyrrolo-[2,3-b]pyridine and 204 mg (1,3 mmol) of 2-chloroacetophenon in 10 ml of CH$_3$CN was refluxed for 48 h. The reaction mixture was cooled to room temperature and stirred for one hour. The precipitate was filtered off to give 260 mg (67%) of 3chloro-2-methyl-7-phenacylpyrrolo-[2,3-b]pyridinehydrochloride.

($^1$H-NMR, 500 MHz, DMSO-d$_6$) 2.50(s,3H), 6.62(s,2H), 7.68(t,2H), 7.78(m, 2H), 8.11(d, 2H), 8.62(d, 1H), 8.70(d, 1H).

Example 10

2,3-Dimethyl-7-(p-bromophenacyl)pyrrolo[2,3-b]pyridine, hydrobromide

This compound was prepared by reacting 2,3-dimethylpyrrolo [2,3-b]pyridine with p-bromophenacyl bromide following the procedure in example 8.
Yield: 92%.

($^1$H-NMR, 300 MHz, DMSO-d$_6$) 2,29(s, 3H), 2,41(s, 3H), 6,47(s, 2H), 7,63(dd, 1H), 7,92(m, 2H), 8,03(m, 2H), 8,43(d, 1H), 8,64(d, 1H), 12,8(b, 1H)

Example 11

2,3-Dimethyl-7-(2-phenyl-2-hydroxyethyl)pyrrolo[2,3-b]pyridine.

A solution of 2,3-dimethyl-7-phenacylpyrrolo[2,3-]pyridine (120 mg, 0.4 mmol) in 3 ml MeOH was treated twice with 20 mg NaBH$_4^-$ portions and allowed to react for 2h at room temperature. The solvent was evaporated and the residue partitioned between 50 ml CH$_2$Cl$_2$ and 25 ml 2.5% NaOH. The organic layer was separated, washed with 10 ml 2M HCl, dried over MgSO$_4$ and evaporated leaving 113 mg (94%) title compound as the hydrochloride.

($^1$H-NMR, 300 MHz, DMSO-d6). 2.26(s,3H), 2.48(s,3H), 4.81(dd, 1H), 4.97(dd, 1H), 5.15(dd, 1H), 5.91(dd, 1H), 7.37(m, 3H), 7.53(t,1H), 7.61(d,2H), 8.51(t,2H), 13.4(b, 1H).

Example 12

3-Chloro-2-methyl-7-(2-phenyl-2-hydroxyethyl)pyrrolo[2,3-b]pyridine

To a solution of 120 mg (0,37 mmol) of 3-chloro-2-metyl-7-phenacylpyrrolo[2,3-b]pyridine hydrochlorid in 2 ml methanol was added 30 mg (0,79mmol) of sodium borohydride. The mixture was stirred for 20 h at room temperature. The solvent was evaporated and the residue was partitioned between 2 ml of 0,2M hydrochloric acid and 2 ml of ethyl acetate. The aqueos layer was basified by addition of 2M sodium hydroxide and extracted twice with 2 ml of methylene chloride. The combined organic phase was dried over sodium sulfate and the solvent was evaporated. The residue was treated with acetonitrile and the precipitate was filtered off to give 20 mg (19%) 3-chloro-2-methyl-7-(2-phenyl-2-hydroxyethyl)pyrrolo-[2,3-b]pyridine.

($^1$H-NMR, 500 MHz, CDCl$_3$) 2.55(s,3H), 4.76(dd, 1H), 4.91(dd, 1H), 5.32(dd, 1H), 6.73(dd, 1H), 7.20(d,1H), 7.25(m, 1H), 7.28(m,4H), 7.88(d, 1H).

Example 13

2,3-Dimethyl-7-(2-(p-cyanophenyl)-2-hydroxyethyl)-pyrrolo [2,3-b]pyridine.

The title compound was prepared on a 0.4 mmol scale mainly according to example 11 above yielding 68 mg (61%) pure title compound as a yellow solid.

($^1$H-NMR, 300 MHz, CDCl$_3$). 2.27(s,3H), 2.51(s,3H), 4.73(dd,1H), 4.91(dd, 1H), 5.36(dd, 1H), 6.65(t,1H), 7.03(d, 1H), 7.40(d,2H), 7.56(d,2H), 7.78(d, 1H).

Example 14

2-Methyl-7-phenacyl-pyrrolo[2,3-b]pyridine hydrochloride

2-Methyl-pyrrolo[2,3-b]pyridine (0.5 g, 3.78 mmol), phenacyl chloride ( 0.62 g, 4.0 mmol ) and acetonitrile (10 ml) were refluxed for 12 h. The solid was filtered off and washed with cold carbon tetrachlorid (2 ml). The crude product was recrystallized from chloroform/ether, 1:1, to give 0.95 g (88%) title compound.

($^1$H NMR, 300 MHz, DMSO-d$_6$); 1.25(s,3H), 6.65(s,2H), 6.70(s,1H), 7.65(m, 3H), 7.80(t,1H), 8.10(d,2H), 8.50(d, 1H), 8.65 (d, 1H).

Example 15

2,3-Dimethyl -7(2-trifluoromethylphenacyl)-pyrrolo[2,3-b]pyridine hydrobromide

The title compound was made according to the general method from Example 14. 2,3 -dimethyl-pyrrolo[2,3-b]pyridine (438 mg, 3 mmol), 2-trifluoromethylphenacyl bromide (798 mg, 3 mmol ) in acetonitrile (5 ml). Yield 0.44 g (36% ).

($^1$H-NMR, 300 MHz, DMSO-d$_6$), 2.45(s,3H), 2.50(s,3H), 6.55(s,2H),7.65(t,1H), 7.95(t,1H), 8.05(m,2H), 8.40(d,2H), 8.65 (d, 1H).

Example 16

3-Bromo-2-methyl-7-phenacyl-pyrrolo[2,3-b]pyridine hydrobromide.

The title compound was made according to the general method from Example 14. 3-bromo-2-methyl-pyrrolo[2,3-b]pyridine (250 mg, 1.19 mmol) phenacyl bromide (200 mg, 1.3 mmol) in acetonitrile (50 ml). Yield 146 mg (37%).

($^1$H-NMR, 300 MHz, DMSO-d$_6$), 2.5(s,3H), 6.7 ( s, 2H), 7.65(t, 1H), 7.75(m,3H), 8.1(d,2H) , 8.6(m,2H).

Example 17

2-Chloro-3-methyl-7-phenacylpyrrolo-[2,3-b]pyridine. Hydrochloride.

A solution of 1.2 g (7.2mmol) 2 -chloro-3 -methylpyrrolo [2,3 b]pyridine and 1.3 g (8.7 mmol) phenacyl chloride in 50 ml acetonitrile was refluxed for 48 h. The solvent was allowed to cool and the precipitated product was filtered off and dried, affording 1,5 g (65%) pure title compound.

($^1$H-NMR, 300 MHz, CDCl$_3$) 2.35(s,3H), 7.0(s,2H), 7.4(dd, 1H), 7.55(t,2H), 7.65(t,1H), 7.8(d, 1H) , 8.2–8.3(m,3H).

Example 18

2-Chloro-3-methyl-7-(2-phenyl-2-hydroxyethyl)pyrrolo[(2,3-b]pyridine

A solution of 0,8 g (2,5 mmol) 2-chloro-3-methyl-7-phenacylpyrrolo[2,3-b]pyridine in 50 ml methanol was cooled to 0° C. It was then treated with NaBH$_4$-portions until all starting material had reacted. (The reaction was followed by TLC). The solvent was evaporated and the residue partitioned between methylene chloride and water. The organic layer was separated, dried over Na$_2$SO$_4$ and evaporated. The residue was treated with ether and isolated by filtration to give 0,6 g (84%) of the title compound as white solid.

($^1$H-NMR, 300 MHz, CD$_3$OD) 2.3(s,3H), 4.5(dd, 1H), 4.9(dd, 1H), 5.25(dd, 1H), 6.95(t,1H), 7.25–7.4(m, 3H), 7.5(d,2H), 7.85(d, 1H), 8.0(d, 1H).

Example 19

3-Methoxy-2-methyl-7-phenacyl pyrrolo[2,3-b]pyridine. Hydrochloride.

A solution of 0,75 g (4,6 mmol) 3-methoxy-2-methylpyrrolo[2,3-b]pyridine and 0,75 g (4,8 mmol) phenacyl chloride in 50 ml acetonitrile was refluxed for 14 h. Working up in the same manner as ex. 17 gave 0,5 g (34%) of the desired product.

($^1$H-NMR, 300 MHz, CDCl$_3$) 2.55(s,3H), 3.95(s,3H), 7.0(s,2H), 7.35 (t, 1H), 7.5(t,2H), 7.6(t,1H), 7.9(d, 1H), 8.25(d,2H), 8.35 (d, 1H).

Example 20

2-Methoxymethyl-3-methyl-7-phenacyl pyrrolo[2,3-b]pyridine. Hydrochloride.

A solution of 0,13 g (0,74 mmol) 2-methoxymethyl-3-methylpyrrolo[2,3-b]pyridine and 0,16 g (1,1 mmol) phenacyl chloride in 20 ml acetonitrile was refluxed for 15 h. Working up in the same manner as ex. 17 gave 0,05 g (20%) of the title compound.

($^1$H-NMR, 300 MHz, CDCl$_3$), 2.4(s,3H), 3.45(s,3H), 4.8(s,2H), 7.05(s,2H), 7.4(dd, 1H), 7.55(t,2H), 7.65 ( t, 1H), 7.85 (d, 1H), 8.25(d,2H), 8.35(d, 1H).

Example 21

2-Chloro-3-methyl-7-(p-fluorophenacyl)pyrrolo[2,3-b]pyridinehydrochloride

A solution of 1,2 g (7,2 mmol) 2-chloro-3-methylpyrrolo[2,3-b]pyridine and 1,5 g (8,7 mmol) p-fluorophenacyl chloride in 50 ml acetonitrile was refluxed for 48 h. The mixture was allowed to cool and the precipitated product filtered off. The solid was treated with ethyl acetate and filtered off again affording 1,4 g (57%) of the desired product.

($^1$H-MNR, 300 MHz, CD$_3$OD) 2.4(s,3H), 6.45(S,2H), 7.4(dd,2H), 7.65(dd, 1H), 8.25(dd, 2H), 8.45(cl, 1H), 8.7(d, 1H).

Example 22

2-Chloro-3-methyl-7-(2-(p-fluorophenyl)-2-hydroxyethyl)pyrrolo [2,3-b]pyridine.

A solution of 1,0 g (2,8 mmol) of 2-chloro-3-methyl-7-(p-fluorophenacyl)pyrrolo [2,3-b]pyridine hydrochloride in 50 ml methanol was treated with NaBH in the same manner as ex. 18 to give 0,85 g (99%) of the title compound as white solid.

($^1$H-NMR, 300 MHz, CD$_3$OD) 2.3(s,3H), 4.5(dd,1H), 4.9(dd, 1H), 5.3(dd, 1H), 6.95(t,1H), 7.1(t,2H), 7.45–7.55(m,2H), 7.8(d, 1H), 8.0(d, 1H).

Example 23

2-Chloro-3-cyanomethyl-7-phenacylpyrrolo[2,3-b]pyridine

A solution of 0,66 g (3,4 mmol) 2-chloro-3-cyanomethyl-pyrrolo[2,3-b]pyridine, and 0,65 g (3,8 mmol) phenacyl bromide in 40 ml acetonitrile was refluxed for 20 h. The mixture was allowed to cool and the precipitated product was filtred off and recrystallized from acetonitrile. Chromatography on silica gel eluting with ethyl acetate gave the desired product (0,094g, 9%).

($^1$H-NMR, 300 MHz, CDCl$_3$) 3.9(s,2H), 6.15(s,2H), 7.05(t,1H), 7.5–7.65(m,3H), 7.7(t,1H), 8.1(d,2H), 8.25(d, 1H).

Example 24

2,3-Dimethyl-7-(o-methylthiophenacyl)pyrrolo[2,3-b]pyridinehydrobromide.

A solution of 0,2 g ( 1,4 mmol) 2,3-dimethylpyrrolo[2,3-b]pyridine and 0,34 g (1,4 mmol) o-methylthiophenacyl bromide was stirred at room temperature for 4 h. The precipitated product was filtred off and dried affording 0,11 g (20%) of the title compound.

($^1$H-NMR, 300 MHz, CDCl$_3$) 2.25(s,3H), 2.45(s,3H), 2.6(s,3H), 6.9(s,2H), 7.35–7.45(m,3H), 7.6(t,1H), 7.75(d, 1H), 8.25(d, 1H), 8.65(d,1H).

Example 25

3-Hydroxy-2-methyl-7-phenacylpyrrolo[2,3-b]pyridine.

To a solution of 0,05 g (0,16 mmol) 3-methoxy-2-methyl-7-phenacyl pyrrolo[2,3-b]pyridine in 10 ml methylene chloride was added 0,5 ml (0,2 mmol) bortribromide in methylene chloride (1M) at RT. The reaction was followed by T.L.C. The mixture was stirred 20 h. and was evaporated. The product was solved in 2 ml methylene chloride/methanol 10/1 and a small amount of water and chromatography of this mixture on silica gel eluting with methylene chloride/methanol 10/1 gave the product as an oil. The oil was treated with ether to give the title product as yellow solid.

($^1$H-NMR, 300 MHz, DMSO-d$_6$), 2.35(s,3H), 6.45(s,2H), 7.55(bs,1H), 7.7(t,2H), 7.8(t,1H), 8.15(d,2H), 8.4(d, 1H), 8.6(d, 1H).

Example 26

2,3-Dimethyl-5-trifluoromethyl-7-phenacylpyrrolo[2,3-b]pyridine

A solution of 0,1 g (0,47 mmol) 2,3-dimethyl-5-trifluoromethyl-pyrrolo[2,3-b]pyridine and 0,13g (0,84 mmol) 2-chloroacetophenone in 5 ml acetonitrile was refluxed for 48 h. The solvent was evaporated. Chromatography on silica gel eluting with methylene chloride and methanol (100:5) gave the desired product. (0,023 g 15%).

($^1$H-NMR, 300 MHz, CDCl$_3$) 2.3(s,3H), 2.45(s,3H), 6.15 (s, 2H), 7.55(t,2H), 7.65(t,1H), 7.75(s,1H), 7.95(s,1H), 8.05(d, 2H).

Example 27

2,3Dimethyl-7-(p-cyanophenacyl)pyrrolo[2,3-b]pyridine.

A solution of 2,3-dimethylpyrrolo[2,3-b]pyridine (146 mg, 1 mmol) and p-cyanophenacyl bromide (248 mg, 1.1 mmol) in 3 ml CH$_3$CN was refluxed for 1.5 h. The mixture was allowed to cool and the precipitated product filtered off and washed with a small volume of ice cold CCl$_4$ affording 313 mg (85%) pure title compound as the hydrobromide salt.

($^1$H-NMR, 300 MHz, CDCl$_3$) 2.30(s,3H), 2.50(s,3H), 7.10(s,2H), 7.40(dd,1H), 7.68(d,2H), 8.00(d, 1H), 8.29(d,1H), 8.39(d,2H), 13.6(b,1H).

Example 28

2,3-Dimethyl-7-(p-fluorophenacyl)pyrrolo[2,3.-b]pyridine.

The title compound was prepared on a 1 mmol scale from 2,3-dimethylpyrrolo[2,3-b]pyridine and p-fluorophenacyl bromide following the procedure in example 27 above yielding 260 mg (64%) pure product as the hydrobromide.

¹H-NMR, 300 MHz, CDCl₃), 2.28(s,3H) 2.56(s,3H), 6.99(s,2H), 7.18(m,2H), 7.38(dd, 1H), 7.83 (d, 1H), 8.24 (d, 1H), 8.35(m,2H), 13.8(b,1H).

Example 29

2,3-Dimethyl-7-(p-metoxyphenacyl)pyrrolo[2,3-b]pyridine.

The title compound was prepared from 2,3-dimethylpyrrolo [2,3-b]pyridine (120 mg, 0.82 mmol) and p-methoxyphenacyl bromide (207 mg, 0.90 mmol) following the procedure in example 27 above furnishing 223 mg (73%) pure hydrobromide as a light yellow solid.

(¹H-NMR, 300 MHz, CDCl₃) 2.27(s,3H), 2.58(s,3H), 3.88(s,3H), 6.91(s,2H), 7.00(m, 2H), 7.37 (dd, 1H), 7.81(d, 1H), 8.22(d, 1H), 8.28(m,2H).

Example 30

2,3-Dimethyl-7- (m-methoxyphenacyl)pyrrolo[2,3-b]pyridine.

The title compound was prepared on a 0.9 mmol scale fr 2,3-dimethylpyrrolo[2,3-b]pyridine and m-methoxyphenacyl bromide in the same manner as described in example 27 giving 228 mg (70%) pure product as the hydrobromide.

(¹H-NMR, 300 MHz, CDCl₃ ). 2.27(s,3H), 2.57(s,3H), 3.91(s,3H), 6.97(s,2H), 7.18(dd, 1H), 7.37 (dd, 1H), 7.43 (t, 1H), 7.75 (bt, 1H), 7.79 (d, 1H), 7.89(d, 1H), 8.22 (d, 1H).

Example 31

2,3-Dimethyl-7-(o-methoxyphenacyl)pyrrolo[2,3-b]pyridine.

The title compound was prepared on a 1 mmol scale from 2,3-dimethylpyrrolo[2,3-b]pyridine and o-methoxyphenacyl bromide in the same manner as described in example 27 yielding 244 mg (71%) pure hydrobromide as a light yellow solid.

(¹H-NMR, 300 MHz, CDCl₃). 2.26(s,3H), 2.60(s,3H), 4.20(s,3H), 6.71(s,2H), 7.04(m, 1H), 7.11(d, 1H), 7.35 (dd, 1H), 7.59 (m, 1H) , 7.69 (d, 1H), 7.95 (dd, 1H), 8.20 (d, 1H).

Example 32

2,3-Dimethyl-7-(2,4-difluorophenacyl)pyrrolo[2,3-b]pyridine.

The title compound was prepared on a 1 mmol scale from 2,3-dimethylpyrrolo[2,3 -b]pyridine and o,p-difluorophenacyl bromide following the procedure described in example 27 giving 194 mg (56%) pure hydrochloride as a yellow solid.

(¹H-NMR, 300 MHz, CDCl₃) 2.27(s,3H), 2.53(s,3H), 6.76(d,2H), 6.96 (m overlapping signals, 2H), 7.34(dd, 1H), 7.80(d, 1H), 8.15(m, 1H), 8.22(d, 1H), 14.9(b, 1H).

Example 33

5-Chloro-3-cyanomethyl-2-methyl-7-phenacylpyrrolo[2,3-b]pyridine

A mixture of 5-chloro-3-cyanomethyl-2-methyl-pyrrolo[2,3-b]pyridine (147 mg, 0.7 mmol) and phenacylbromide (142 g, 7 mmol) in 12 ml CH₃CN was refluxed for 22h. The reaction mixture was cooled and precipitated title compound was collected and washed with small portions of ice cold diethyl ether. Treatment of the filtrate with diethyl ether afforded a second and third lot of pure title compound. Total yield 257 mg (91%) calculated as the hydrobromide.

(¹H-NMR, 300 MHz, DMSO-d₆). 2.53(s,3H), 4.24(s,2H), 6.50(s,2H), 7.70(t,2H), 7.83(t,1H), 8.10(d,2H), 8.90(d, 1H), 9.042 (s,1H ).

Example 34

2,3-Dimethyl-7-[2-phenyl-2-methoxyethyl)-pyrrolo[2,3-b]pyridine

A solution of 2,3-dimethyl-7-(2-phenyl-2-hydroxyethyl)pyrrolo[2,3-b]pyridine (as the base) (266 mg, 1.0 mmol) in 25 ml dry THF was deaerated and treated with 55% NaH dispersion in oil (48 mg, 1.1 mmol) for 30 min. Methyl iodide (62 μl, 1.0 mmol) was added and allowed to react for 50 min. The solvent was evaporated and the residue partitioned between 100 ml CH₂Cl₂ and 20 ml 5% NaOH. The organic layer was dried over MgSO₄ and evaporated. The residue was chromatographed (silica, CH₂Cl₂ saturated with NH₃). Pure fractions were pooled and evaporated leaving a gum which partly crystallized. Trituation with diethyl ether furnished 207 mg (65%) pure title compound.

(¹H-NMR, 300 MHz,CDCl₃). 2.29(s,3H), 2.54(s,3H), 3.14(s,3H), 4.41(dd, 1H), 4.86(dd, 1H), 4.99(dd, 1H), 6.64(t,1H), 7.38 (overlapping signals, 6H), 7.75(d, 1H).

Example 35

2,3-Dimethyl-7-(o-nitrophenacyl)pyrrolo[2,3-b]pyridine.

The title compound was prepared on a 5 mmol scale from 2,3-dimethylpyrrolo[2,3-b]pyridine and o-nitrophenacyl bromide in the same manner as described in example 27 yielding 1.3 g (66%) pure hydrobromide as a yellow solid. Reprocessing of the motherliquor gave additional material.

(¹H-NMR, 300 MHz, DMSO-d₆). 2.30(s,3H), 2.47(s,3H), 6.38(s,2H), 7.68(dd, 1H), 7.97(dt,1H), 8.08(t,1H), 8.21(dt,2H), 8.37(d, 1H), 8.67(d, 1H), 12.9(b,1H).

Example 36

2,3-Dimethyl-7-(o-aminophenacyl)pyrrolo[2,3-b]pyridine.

2,3-Dimethyl-7-(o-nitrophenacyl)pyrrolo[2,3-b]pyridine (1.02 g, 2.6 mmol) was dissolved in 39 ml abs. EtOH and treated with SnCl₂.2H₂O (4.75 g, 21 mmol) and 13 ml conc HCl at 80° C. for 3h. The reaction mixture was allowed to cool and then partitioned between 500 ml 2M HCl and 250 ml CH₂Cl₂. The organic layer was extracted with additional 150 +50 ml 2M HCl. The aqueous layers were combined and washed with 400 ml diethyl ether. The pH was adjusted to 12 and the basified product extracted with 800+400+200 ml CH₂Cl₂. The latter organic layers were combined, dried over MgSO₄, and evaporated leaving 340 mg (46%) pure amine as an intense yellow solid.

(¹H-NMR, 300 MHz, CDCl₃). 2.28(s,3H), 2.47(s,3H), 6.09(s,2H), 6.21(b,2H), 6.71(m,2H), 6.81(t,1H), 7.33(m,2H), 7.82(d,1H), 7.88(d, 1H).

Example 37

2,3-Dimethyl-7-[p-methylphenacyl)pyrrolo[2,3-b]pyridine.

A solution of 2,3-dimethylpyrrolo[2,3-b]pyridine (0.16 g, 1.1 mmol) and p-methylphenacyl bromide (0.26 g, 1.2 mmol) in 4.5 ml CH₃CN was warmed to reflux which was enough to initiate crystallisation of the product as a light yellow solid. The precipitate was isolated as described in example 27 furnishing 0.29 g (74%) pure hydrobromide.

($^1$H-NMR, 300 MHz, CDCl$_3$). 2.27(s,3H), 2.41(s,3H), 2.57(s,3H), 6.94(s,2H), 7.32(d,2H), 7.37(dd, 1H), 7.80(d, 1H), 8.17(d,2H), 8.23(d, 1H), 13.8(b, 1H).

Examples 38 and 39

(R and S)-2,3-dimethyl-7-(2-phenyl-2-hydroxyethyl)-pyrrolo-[2,3-b]pyridinehydrochloride.

R(-)-2-methoxy-2-phenylacetic acid was dissolved in 3 ml SOCl$_2$ at 0° C. and allowed to react for 4h at room temperature. The excess SOCl$_2$ was evaporated and the residue treated with a solution of a racemic mixture of 2,3-dimethyl-7-(2-phenyl-2-hydroxyethyl)pyrrolo[2,3-b]pyridine prepared according to Example 11 (302 mg, 1.0 mmol) and Et$_3$N (279 μl, 2.0 mmol) in 20 ml CH$_2$Cl$_2$. After reacting for 16h at room temperature the mixture was paritioned between 150 ml CH$_2$Cl$_2$ and 50 ml 2M HCl. The organic layer was collected washed with 50 ml 5% Na$_2$CO$_3$, dried over MgSO$_4$, and evaporated. Diastereomers 1 and 2 were separated by chromatography (silica, CH$_2$Cl$_2$ saturated with NH$_3$/diethyl ether;1/1). Diastereomer 2 was further purified by chromatography (silica, CH$_2$Cl$_2$ saturated with NH$_3$). Yields, 149 mg (36%) and 90 mg (22%) of isomers 1 and 2, respectively. Each isomer (149 mg, 0.36 mmol 1 and 89 mg, 0.21 mmol 2) was dissolved in a few ml of MeOH and LiOH (a 5-fold molar excess) dissolved in a few ml H2O was added and allowed to react for 1 h at room temperature. The solvent was evaporated and each residue partitioned between 100 ml CH$_2$Cl$_2$ and 50 ml 5% Na$_2$CO$_3$. Each organic layer was washed once with 50 ml 2M HCl, dried over MgSO$_4$, and evaporated leaving 100 mg (92%) enantiomer 1 and 52 mg (82%) enatiomer 2.

($^1$H-NMR, 300 MHz, DMSO-d$_6$). Cf. Example 11.

Example 40

2,3-Dimethyl-7-(o-hydroxyphenacyl)pyrrolo[2,3-b]pyridine.

A solution of 2,3-dimethyl-7-(o-methoxyphenacyl)pyrrolo[2,3-b]pyridine (75 mg, 0.2 mmol) in 20 ml CH$_2$Cl$_2$ was cooled to 0° C. and treated with 1M BBr$_3$ in CH$_2$Cl$_2$ (200 μl, 0.2 mmol). After reacting for an additional hour the reaction mixture was poured into a stirred solution of 5% NaHCO$_3$. The aqueous layer was attracted with 50+10 ml CH$_2$Cl$_2$ and the combined organic layers washed With 50 ml 2M HCl (reextraction trice with 10 ml CH$_2$Cl$_2$). The combined organic layers were dried over MgSO$_4$ and evaporated. The residue was chromatographed (silica, CH$_2$Cl$_2$/MeOH; 9/1) affording 35 mg (62%) pure title compound.

($^1$H-NMR 500 MHz, CDCl$_3$) 2 27(s,2H), 2.50(s,3H) 6.40(b,2H), 6.93(b,1H), 6.98(d,1H), 7.14(t,1H), 7.40(b,1H), 7.6(d, 1H), 7.85(b,1H), 8.07(d,1H).

Example 41

2,3-Dimethyl-6-methylthio-7-phenethylpyrrolo[2,3-b]pyridine.

A refluxing solution of 2,3-dimethyl-6-mehylthiopyrrolo[2,3-b]pyridine (100 mg, 0.5 mmol) in 5 ml CH$_3$CN was treated with five portions of phenethyl bromide (85 μl, 1.2 mmol), one each 24 h. The solvent was evporated and the residue chromatographed (silica, CH$_2$Cl$_2$ saturated with NH$_3$/diethyl ether/petroleum ether; 5/2/3) affording 20 mg (13%) pure title compound.

($^1$H-NMR 500 MHz CDCl$_3$) 2.27(s,3H), 2.52(s,3H), 2.53(s,3H), 3.25(m, 2H), 5.10(m, 2H), 6.75(d,1H), 7.25(m, 1H), 7.31 overlapping signals, 4H), 7.68(d,1H).

Example 42

2,3-Dimethyl-7-phenethyl-6-phenethylthiopyrrolo[2,3-b]pyridine hydrochloride

A refluxing solution of 2,3-dimethyl-6-methylthiopyrrolo [2,3-b]pyridine (391 mg, 2.0 mmol) in 9 ml CH$_3$CN was treated with five portions of phenethyl bromide (553 μl, 4.0 mmol), one each 24 h. The solvent was evaporated and the residue chromatographed (silica, CH$_2$Cl$_2$ saturated with NH$_3$/diethyl ether/petroleum ether; 5/2/3). Pure fractions were pooled, diluted to the double volume with CH$_2$Cl$_2$ and washed with 50 ml 2M HCl. The organic layer was dried over MgSO$_4$ and evaporated leaving 221 mg (26%) pure product.

($^1$H-NMR, 500 MHz, CDCl$_3$), 2.29(s,3H), 2.55(s,3H), 2.90(t,2H), 3.16(t,2H), 3.24(m,2H), 5.14(m, 2H), 6.92(d, 1H), 7.13(d,2H), 7.23(overlapping signals, 4H), 7.29 (overlapping signals, 4H), 7.68(d, 1H).

Example 43

2,3-Dimethyl-6-methylthio-7-phenacylpyrrolo[2,3-b]pyridine.

A mixture of 2,3-dimethyl-6-methylthiopyrrolo[2,3-b]pyridine (100 mg, 0.5 mmol) and phenacyl chloride (804 mg, 5 mmol) in 3 ml CH$_3$CN was refluxed for 72 h. The solvent was evaporated and the residue chromatographed (silica, CH$_2$Cl$_2$/MeOH;59/5). Pure fractions were pooled, evaporated, and taken up in 100 ml CH$_2$Cl$_2$. The organic layer was washed with 25 ml 2M HCl, dried over MgSO$_4$, and evaporated leaving 64 mg (35%) pure product as the hydrochloride.

($^1$H-NMR of the free base, 300 MHz, CDCl$_3$). 2.25(s,3H), 2.45(s,3H), 2.53(s,3H), 6.62(b,2H), 7.05(d, 1H), 7.55(m,2H), 7.66(m,1H), 7.85(d,1H), 8.12(m,2H).

Example 44

2,3-Dimethyl-5-methylthio-7-phenacylpyrrolo[2,3-b]pyridine.

The title compound was prepared on a 0.6 mmol scale from 2,3-dimethyl-5-methylthiopyrrolo[2,3-b]pyridine (prepared according to the procedure described for 2,3-dimethyl-6-methylthio-pyrrolo[2,3-b]pyridine) and phenacyl chloride as described in Example 43 yielding 140 mg (63%) pure title compound as the hydrochloride.

($^1$H-NMR, 500 MHz, CDCl$_3$). 2.26(s,3H), 2.57(s,3H), 2.60(s,3H), 6.95(b,2H), 7.60(m,2H), 7.69(m,2H), 8.22(s,1H), 8.30(m,2H).

Example 45

2,3-Dimethyl-5-methylsulfinyl-7-phenacylpyrrolo[2,3-b]pyridine.

A solution of 2,3-dimethyl-5-methylthio-7-phenacylpyrrolo[2,3-b]pyridine (35 mg, 0.1 mmol) in 20 ml CH$_2$Cl$_2$ was cooled to −20° C. an treated with 71% m-CPBA (27 mg, 0.1 mmol) for 30 min. The volume was adjusted 50 ml with CH$_2$Cl$_2$ and the organic layer washed twice with 50 ml 5% Na$_2$CO$_3$ and once with 2M HCl (reextraction trice with 25 ml CH$_2$Cl$_2$). The organic layer was dried over MgSO$_4$ and evaporated leaving 15 mg (41%) pure title compound.

($^1$H-NMR of the hydrochloride, 300 MHz, CDCl$_3$). 2.31(s,3H), 2.59(s,3H), 2.95(s,3H), 7.05(s,2H), 7.54(t,2H), 7.66(t,1H), 8.16(s,1H), 8.25(d,2H), 8.36(s,1H).

Example 46

2,3-Dimethyl-7-(o-carboxyphenethyl)pyrrolo[2,3-b]pyridine.

A solution of 2,3-dimethylpyrrolo[2,3-b]pyridine (554 mg, 3.8 mmol) and o-bromophenethyl bromide (1000 mg, 3.8 mmol) in 11 ml $CH_3CN$ was refluxed for 16 h. The solvent was evaporated and the residue chromatographed (silica, $CH_2Cl_2$/MeOH; 9/1) to give 546 mg enriched product. Pure 2,3-dimethyl-7-(o-bromophenethyl) pyrrolo[2,3-b]pyridine was obtained by a second chromatography (silica, $CH_2Cl_2$ saturated with $NH_3$/petroleum ether; 7/3). A deaerated solution of 2,3-dimethyl-7- (o-bromophenethyl) pyrrolo[2,3-b]pyridine (249 mg, 0.76 mmol) in 25 ml dry THF was cooled to $-78°$ C. and treated with 1.6M n-BuLi in hexane (576 μl, 0.91 mmol). After 3 min a vigurous stream of $CO_2(g)$ was bubbled through the solution. The solution was allowed to warm to room temperature and 1.5 ml $H_2O$ was added. The solvent was evaporated and the residue chromatographed (reversed phase silica, MeOH/$H_2O$; 6/4) yielding 51 mg (23%) pure amino acid.

($^1$H-NMR of the hydrochloride, 300 MHz, $CDCl_3$). 2.22(s,3H), 2.56(s,3H), 3.55(t,2H), 5.07(t,2H), 6.86(d, 1H), 7.04(m, 1H), 7.19(m, 1H), 7.24(m, 1H), 7.83(dd, 1H), 7.91(d, 1H), 8.09(d,1H).

Example 47

5-Bromo-2,3-dimethyl-7-phenacyl pyrrolo[2,3-b]pyridine.

A solution of 5-bromo-2,3 -dimethyl-pyrrolo [2,3-b]pyridine (prepared in a similar manner as 6-bromo-2,3-dimethyl-pyrrolo[2,3-b]pyridine (200 mg, 0.9 mmol) and phenacyl bromide (200 mg, 1.3 mmol) in 15 ml $CH_3CN$ was refluxed for 16 h. The mixture was allowed to cool and the precipitated product filtered off and washed with a small volume of diethyl ether affording 243 mg (72%) pure title compound as the hydrochloride.

($^1$H-NMR, 500 MHz, DMSO-$d_6$). 2.28(s,3H), 2.43(s,3H), 6.58(s,2H), 7.68(t,2H), 7.81(t,1H), 8.09(d,2H), 8.84(s,1H), 8.95(s,1H).

Example 48

5-Cyano-2,3-dimethyl-7-phenacyl pyrrolo[2,3-b]pyridine.

A mixture of 5-cyano-2,3-dimethyl-pyrrolo [2,3-b]pyridine (77 mg, 0.5 mmol ) and phenacyl chloride (650 mg, 4.2 mmol ) in 12 ml $CH_3CN$ was refluxed for 62 h. The mixture was basified with a saturated $Na_2CO_3$ solution and extracted with $CH_2Cl_2$. The organic layer was dried over $MgSO_4$ and evaporated. The residue was chromatographed (silica, $CH_2Cl_2$/diethyl ether;7/3) yielding 34 mg (26%) pure title compound.

(DI-MS, EI at 70 eV) m/z 289 (25) , 260 (15), 171 (38), 170 (50), 146 (32), 105(100).

($^1$H-NMR, 300 MHz, $CDCl_3$) 2.26(s,3H), 2.43(s,3H), 6.09(s,2H), 7.54(t,2H), 7.68(t,1H), 7.75(d, 1H), 7.89(d, 1H), 8.06(overlapping signals, 2H).

Example 49

Preparation of 3-cyanomethyl-2-methyl-7-phenacyl-pyrrolo[2,3-b]pyridine hydrochloride.

A solution of 1.0 g (5.8 mmol) of 3-cyano-methyl-2-methyl pyrrolo[2,3-b]pyridine and 1.08 g (7.0 mmol) of phenacyl chloride in 50 ml acetonitrile was refluxed for 14 h. Working up in the same manner as described in example 17 gave 0,5 g 58% of the desired title compound.

($^1$H-NMR, 300 MHz, DMSO-$d_6$), 2.50(s,3H), 4.25(s,2H), 6.62(s,2H), 7.6–7.83(m, 4H), 8.10(d,2H), 8.56(d, 1H), 8.79(d,1H).

Example 50

Preparation of 3-(1-pyrazolo)methyl-2-methyl-7-phenacyl pyrrolo [2,3-b]pyridine.

A solution of 30 mg (0.14 mmol) of 3-(1-pyrazolo)-methyl-2-methyl pyrrolo[2,3-b]pyridine and 32 mg (0.21 mmol) of phenacyl chloride in 1 ml acetonitrile was refluxed for 10 h. The solvent was evaporated and the crude product was treated with acetonitrile and the product was isolated by filtration. The product was partitioned between methylene chloride and a saturated sodium bicarbonate solution. The organic layer was dried over sodium sulfate and the solvent was evaporated to give 18 mg (39%) of the title compound.

($^1$H-NMR, 300 MHz, $CD_3OD$), xHCl, 2.60(s,3H), 5.60(s,2H), 6.32(t,1H), 6.42(b,2H), 7.5-7.8 (m,6H), 8.15(m,2H), 8.33(d,1H), 8.49 (d,1H).

Example 51

Preparation of 3-cyanomethyl-2-methyl-7-(4-fluorophenacyl) pyrrolo[2,3-b]pyridine hydrochloride.

A solution of 7 5 mg (0.44 mmol) of 3-cyanomethyl-2-methyl-pyrrolo [2,3 -b]pyridine and 99 mg(0.57 mmol) of 4-fluorophenacyl chloride in 1 ml acetonitrile was refluxed for 48 h. The solvent was evaporated and the residue was treated with 0.4 ml acetonitrile. After filtration the solid was treated with 0,3 ml methanol and 0,4 ml acetonitrile to give 75 mg (55% ) of the title compound.

($^1$H-NMR, 500 MHz, DMSO-$d_6$), 2.50(s,3H), 4.25(s,2H), 6.62(s,2H), 7.53(m, 1H), 7.75(m, 1H), 8.20(dd,2H), 8.55(d,1H), 8.80(d, 1H).

Example 52

Preparation of 2,3-dimethyl-7(2-(2-acetaminophenyl)-ethyl)pyrrolo[2,3-b]pyridine hydrobromide.

A solution of 73 mg (0,5 mmol) 2,3 dimethylpyrrolo[2,3-b]pyridine and 122 mg (0,5 mmol) of (2-bromoethyl)acetanilide in 2 ml acetonitrile was refluxed for 10 h. The solvent was evaporated and the crude product was treated with 5 ml petroleum ether:ether 1:1 and the insoluble fraction was treated with ether. The etheral layer was separated from the oily residue, which crystallized from acetronitrile and gave 15 mg (7,7%) of the title compound.

($^1$H-NMR, 300 MHz, $CDCl_3$), 2.20(s,3H), 2.38(s,3H), 2.42(s,3H), 3.38(t,2H), 5.08(t,2H), 6.48(m, 1H), 6.73(m, 1H), 7.08(m, 1H), 7.23-7.35 (m,2H) , 8.09(d,1H) , 8.55(m, 1H), 10.1(s,1H).

Example 53

Preparation of 2,3-dimethyl-7(2.6-difluorophenacyl)-pyrrolo [2,3 -b ]pyridine hydrobromide.

A solution of 100 mg (0.68 mmol) 2,3-dimethylpyrrolo[2,3-b]pyridine and 193 mg (0.82 mmol) 2,6-difluorophenacyl bromide in 2 ml acetonitrile were refluxed for 3 h. Working up in the same manner as described in example 17 gave 145 mg (54% ) of the desired product.

($^1$H-NMR, 300 MHz, $CDCl_3$) 2.28(s,3H), 2.62(s,3H), 6.72(s,2H), 7.07(m,2H), 7.38 (m,1H), 7.58(m, 1H), 7.73(d,1H), 8.24(d, 1H).

Example 54

Preparation of 3-thiocyano-2-methyl-7-phenacylpyrrolo[2,3-b]pyridine hydrochloride A solution of 100 mg (0.53 mmol) of 3-thiocyano-2-methyl pyrrolo [2,3-b]pyridine and 122 mg (0.79 mmol) of phenacyl chloride in 3 ml acetonitrile: dimethylformamide 2:1 was warmed at 70° C. for 36 h. The reaction mixture was cooled to room temperature and the acetonitrile was evaporated. To the residue was added 10 ml diethyl ether. The precipitated product was filtered off and washed with acetonitrile giving 37 mg (23%) of the title compound.

($^1$H-NMR, 300 MHz, DMSO-d$_6$). 2.65(s,3H), 6.66(s,2H), 7.7(m,2H), 7.79–7.9 (m,2H), 8.11(d,2H), 8.68(d,1H), 8.85(d,1H).

Example 55

2-(p-bromophenyl)-3-methyl-7-phenacyl pyrrolo[2,3-b]pyridine

The title compound was prepared from 2-(p-bromophenyl)-3-methyl-pyrrolo-[2,3-b]pyridine and phenacylbromide on a 1.7 mmol scale according to the procedure described in example 8 yielding 620 mg (74%).

($^1$H-NMR, 500 MHz, CDCl$_3$) 2.55 (s,3H), 7.35 (s, 2H), 7.50 (t, 1H), 7.60 (t, 2H), 7.65 (d, 2H), 7.70 (t, 1H), 7.85 (m, 3H), 8.35 (d, 2H), 8.45 (d, 1H).

Example 56

Methyl-p[3-methyl-7-phenacyl pyrrolo[2,3-b]-pyridine-2-yl]benzoate.

The title compound was prepared from methyl-[p-(-3-methylpyrrolo[2,3-b]-pyridine)-2]yl benzoate and phenacylbromide on a 0.4 mmol scale according to the procedure described in example 8 yielding 70 mg (46%).

($^1$H-NMR, 300 MHz, CDCl$_3$). 2.55 (s, 3H), 3.90 (s, 3H), 6.15 (s, 2H), 6.90 (t, 1H), 7.55 (m, 3H), 7.65 (m, 1H), 8.0 (m, 5H), 8.15 (m, 2H).

Example 57

Isopropyl-[p(3-methyl-7-phenacyl-pyrrolo[2,3-b]pyridine)-2]yl benzoate

The title compound was prepared from isopropyl-[p-(3-methyl-pyrrolo[2,3-b]-pyridine) -2]yl benzoate and phenacylbromide on a 0.2 mmol scale according to the procedure described in example 8 yielding 25 mg (30%).

($^1$H-NMR, 300 MHz, CDCl$_3$). 1.35 (s, 3H), 1.40 (s, 3H), 2.55 (s, 3H), 5.25 (m, 1H), 6.15 (s, 2H), 6.85 (t, 1H), 7.55 (m, 3H), 7.65 (t, 1H), 8.05 (m, 5H), 8.15 (d, 2H).

Example 58

3-Methyl-2-phenyl-7-phenacyl pyrrolo[2,3-b]pyridine

The title compound was prepared from 3-methyl-2-phenylpyrrolo[2,3-b]pyridine and phenacylbromide on a 4 mmol scale according to the procedure described in example 8 yielding 1.58 g (97%).

($^1$H-NMR, 500 MHz, CDCl$_3$). 2.24 (s, 3H), 7.39–7.56 (several overlapping signals, 8H), 7.65 (t, 1H), 7.87 (d, 1H), 7.93 (overlapping d, 2H), 8.33 (overlapping d, 2H), 8.39 (d, 1H), 13.6 (b, 1H).

Example 59

3-Methyl-2-(p-methylphenyl)-7-phenacylpyrrolo[2,3-b]pyridine

The title compound was prepared from 3-methyl-2-(p-methylphenyl)-pyrrolo[2,3-b]pyridine and phenacyl bromide on a 3 mmol scale according to the procedure described in example 8 yielding 1.21 g (96%).

($^1$H-NMR, 500 MHz, CDCL$_3$). 2.37 (s, 3H), 2.52 (s, 3H), 7.29 (d, 2H), 7.37 (s, 2H), 7.43 (dd, 1H), 7.53 (t, 2H), 7.63 (t, 1H), 7.81 (d, 2H), 7.86 (d, 1H), 8.33 (overlapping signals, 3H), 13.5 (b, 1H).

Example 60

2-(p-Methoxyphenyl)-3-methyl-7-phenacylpyrrolo[2,3-b]pyridine

The title compound was prepared from 2-(p-methoxyphenyl)-3-methyl-pyrrolo[2,3-b]pyridine and phenacylbromide on a 10 mmol scale according to the procedure described in example 8 yielding 4.02 g (92% ).

($^1$H-NMR, 300 MHz, CDCl$_3$). 2.50 (s, 3H), 3.83 (s, 3H), 7.00 (d, 2H), 7.36 (s, 2H), 7.42 (dd, 1H), 7.53 (t, 2H), 7.63 (t, 1H), 7.82 (d, 1H), 7.91 (d, 2H), 8.33 (overlapping signals, 3H), 13.5 (b, 1H).

Example 61

2,3-dimetyl-7-(2-phenyl-2-methoxyiminoetyl)-pyrrolo[2,3-b]pyridine (E and Z isomers)

A mixture of 2,3-dimethyl-7-phenacylpyrrolo[2,3-b]pyridine hydrochloride (301 mg, 1 mmol) and methoxyamine hydrochloride (460 mg, 5 mmol) in 3 ml MeOH and 4.5 ml pyridine was allowed to react for 5 days at room temperature. The methanol was evaporated and the residue partitioned between 150 ml CH$_2$Cl$_2$ and 50 ml 2M HCl. The organic layer was collected, dried over MgSO$_4$, and evaporated, Chromatography (silica, CH$_2$Cl$_2$/MeOH;92.5/7.5) afforded 179 mg and 74 mg of each isomer, respectively.

Each isomer was dissolved in 100 ml CH$_2$Cl$_2$ and washed with 20 ml 2M HCl, dried over MgSO$_4$, and evaporated leaving 198 mg (60%) of isomer 1 and 70 mg (21%) of isomer 2. No attempts to establish the stereochemistry was done at this stage.

($^1$H-NMR of isomer 1, 300 MHz, CDCl$_3$). 2.27 (s, 3H), 2.57 (s, 3H), 4.10 (s, 3H), 6.02 (s, 2H), 6.71 (t, 1H), 7.27 (signals overlapping with residual CHCl$_3$, 3H), 7.38 (d, 1H), 7.70 (m, 2H), 7.74 (d, 1H).

($^1$H-NMR of isomer 2, 300 MHz, CDCl$_3$). 2.22 (s, 3H), 2.60 (s, 3H), 3.86 (s. 3H), 6.19 (s, 2H), 7.13 (t, 1H), 7.31 (m, signals overlapping with residual CHCl$_3$, 3H), 7.77 (m, 2H), 7.85 (d, 1H), 7.98 (d, 1H).

Example 62

2-Chloro-3-cyanomethyl-7-(2-phenyl-2-hydroxyethyl) pyrrolo[2,3-b]pyridine

A solution of 2-chloro-3-cyanomethyl-7-phenacylpyrrolo(2,3-b]pyridine (15 mg 0.05 mmol) in 3 ml MeOH was treated with 10 mg NaBH$_4$ and allowed to react for 30 min at room temperature. The solvent was evaporated and the residue partitioned between CH$_2$Cl$_2$ and water. The organic layer was separated, dried over Na$_2$SO$_4$ and evaporated. Chromatography on silica gel eluting with ether gave the desired product (7 mg 46%).

($^1$H-NMR, 300 MHz, CD$_3$OD): 4.0 (s, 2H), 4.55 (dd, 1H), 4.95 (s, 2H), 5.3 (dd, 1H), 7.05 (dd, 1H), 7.25–7.4 (m, 3H), 7.5 (d, 2H), 7.95 (d, 1H), 8.2 (d, 1H)

Example 63

Preparation of 3-(cyanomethyl)-5-fluoro-2-methyl-7-phenacylpyrrolo[2,3-b]pyridine hydrobromide A mixture of 3-(cyanomethyl)-5-fluoro-2-methylpyrrolo [2,3-b]pyridine (0.28 g, 1.5 mmol) and phenacyl bromide 0.32 g, 1.6 mmol) in acetonitrile (5 ml) was refluxed under argon for 3 h, during which time the initial solution was transformed into a suspension. Then the suspension was cooled in an ice bath, filtered and washed with diethyl ether (2×2 ml). The crystalline product was purified by recrystallization from hot acetonitrile to give 0.52 g (90% ) of the title compound.

MS m/z (relative intensity) 307 (14, M+), 306(8), 279(10), 278(20), 105(100), 91(41), 77(97).

Example 64

Preparation of 5-bromo-3-methyl-7-phenacyl-2-phenylpyrrolo[2,3-b]pyridine

5-Bromo-3-methyl-2-phenylpyrrolo[2,3-b]pyridine (0.34 g, 1.2 mmol) and phenacyl bromide (0.49 g, 2.4 mmol) in acetonitrile (20 ml) was refluxed over night to give a clear solution. The cooled solution was alkalized with sodium carbonate solution (10%) and extracted with methylene chloride. Drying over MgSO$_4$, filtration and evaporation of solvents gave a residue which was dissolved in the minimum amount of ethanol. Crystallization was driven to completeness by keeping crystals and mother liquor in the fridge for a few days. Recrystallization by dissolving in hot ethanol and cooling in the fridge over night gave 0.35 g (73%) of yellow crystals.

(free base, $^1$H-NMR, 300 MHz, CDCl$_3$) 2.50 (s, 3H), 6.12 (s, 2H), 7.29 (dr, 1H, J$_1$ 7.5 Hz, J$_2$ 1Hz), 7.40 (t, 2H, J7 Hz), 7.52–7.60 (m, 3H), 7.65–7.70 (m, 1H), 7.86–7.89 (m, 2H), 8.01 (d, 1H, J 2 Hz), 8.12 (d, 2H, J 7 Hz).

Example 65

Preparation of 3-cyanomethyl)-7-phenacyl-2-phenylpyrrolo [2.3-b]pyridine 3-(Cyanomethyl)-2-phenylpyrrolo[2,3-b]pyridine (0.35 g, 1.5 mmol) and phenacyl bromide (0.36 g) in acetonitrile (5 ml) was refluxed for 18 h. The resulting solid product was isolated by filtration and washed with diethyl ether to give pure 3-(cyanomethyl)-7-phenacyl-2-phenylpyrrolo[2,3-b]pyridine hydrobromide (0.46 g, 70%).

($^1$H-NMR, 300 MHz, DMSO-d$_6$). 4.40 (s, 2H), 6.68 (s, 2H), 7.56–74 (m, 8H), 7.78–7.91 (m, 2H), 8.12 (d, 2H, J 7 Hz), 8.74 (d, 1H, J 6 Hz), 9.04 (d, 1H, J 8 Hz).

Example 66

Preparation of 3-(carbamoylmethyl)-7-phenacyl-2-phenylpyrrolo[2.3 -b]pyridine hydrobromide 3-(Carbamoylmethyl)-2-phenylpyrrolo[2,3-b]pyridine (0.35 g, 1.4 mmol) and phenacyl bromide (0.33 g) in acetonitrile (5 ml) were refluxed under argon for 3 h. The resulting yellow suspension was isolated by filtration (0.4 g). The sparingly soluble raw product was dissolved in a mixture of methanol (20 ml) and methylene chloride (480 ml), loaded on a flash chromatography column (SiO$_2$/CH$_2$Cl$_2$:MeOH 96:4), and eluted with a) 1000 ml MeOH:CH$_2$Cl$_2$ 2.5:97.5; b) 1000 ml MeOH:CH$_2$Cl$_2$ 5:95; c) 1000 ml MeOH:CH$_2$Cl$_2$ 1:9 to afford pure 3-(carbamoylmethyl)-7-phenacyl-2-phenylpyrrolo[2,3-b]pyridine which was isolated as its hydrobromide (0.14 g, 22%).

(free base, $^1$H-NMr, 500 MHz, DMSO-d$_6$) 3.70 (s, 2H), 6.33 (s, 2H), 6.68–7.71 (t, 2H, J 7 Hz), 7.27 (t, 1H, J 7.5 Hz), 7.37 (t, 2H, J 7.5 Hz), 7.44 (br s, disappears on addition of D$_2$O), 7.64 (t, 2H, J 8 Hz), 7.77 (t, 1H, J 7 Hz), 7.89 (d, 2H, J 8 Hz), 8.01 (d, 1H, J 6 Hz), 8.17 (D, 2H, J 7.5 Hz), 8.23 (d, 1H, J 7.5 Hz).

Example 67

5-Chloro-3-cyanomethyl-2-methyl-7-(2-phenyl-2-hydroxyethyl) pyrrolo[2,3-b]pyridine The title compound was prepared from 5-chloro-3-cyanomethyl-2-methyl-7-phenacylpyrrolo[2,3-b]pyridine (example 33) and NaBH$_4$ on a 0.33 mmol scale according to the procedure described in example 11. Chromatography of the crude material (silica, CH$_2$Cl$_2$/MeOH; 96/4) afforded 45 mg (42%) pure product.

($^1$H-NMR, 300 MHz, CDCl$_3$). 2.54 (s, 3H), 3.78 (s, 2H), 4.67–4.90 (m, 2H), 5.30 (m, 1H), 7.32 (coinciding signals, 6H), 7.95 (d, 1H).

Example 68

Preparation of 3-cyanomethyl-2-methyl-7-(2,4-difluorophenacyl)pyrrolo[2,3-b]pyridine The title compound was prepared from III and 2-chloro-2′, 4′-difluoroaceto-phenone on a 2.3 mmol scale according to the procedure described in example 8 yielding 570 mg (68%).

($^1$H-NMR, 300 MHz, DMSO-d$_6$). 2.50 (s, 3H), 4.25 (s, 2H), 6.45 (m, 2H), 7.40 (dr, 1H), 7.65 (dr, 1H), 7.75 (t, 1H), 8.10 (m, 1H), 8.55 (d, 1H), 8.80 (d, 1H).

Example 69

Preparation of 3-cyanomethyl-2-methyl-7-(2-methoxyphenacyl)pyrrolo[2,3 -b]pyridine The title compound was prepared from III and w-bromo-2-methoxyacetophenone on a 4,2 mmol scale according to the procedure described in example 8 yielding 0.9 g (54%).

($^1$H-NMR, 300 MHz, DMSO-d$_6$). 2,50 (s, 3H), 4.10 (s, 3H), 4.25 (s, 2H), 6.25 (s, 2H), 7.15 (t, 1H), 7.40 (d, 1H), 7.75 (m, 2H), 7.90 (dd, 1H), 8.60 (d, 1H), 8.80 (d, 1H).

Example 70

Preparation of 3-cyanomethyl-2-methyl-7-(2-hydroxyphenacyl)pyrrolo[2,3-b]pyridine To a deaerated solution of the compound according to example 69 (3.6 g, 8.9 mmol) in 60 ml CH$_2$Cl$_2$ 10.6 ml of 1M BBr$_3$ in CH$_2$Cl$_2$ (10,6 mmol) was added dropwise. The solution was stirred at room temperature for 3h and was then poured into 50 ml of 1 m NaHCO$_3$. The water layer was extracted three times with 100 ml CH$_2$Cl$_2$ and the combined organic layers was washed once with 100 ml 2 m HCl. The organic layer was dried over Na$_2$SO$_4$ and evaporated. The residue was recrystallized from CH$_3$CN affording 2,2 g (73%).

($^1$H-NMR, 500 MHz, DMSO-d$_6$). 2.50 (s, 3H), 4.25 (s, 2H), 6.35 (s, 2H), 7.00 (t, 1H), 7.20 (d, 1H), 7.60 (t, 1H), 7.70 (t, 1H), 7.85 (d, 1H), 8.60 (d, 1H), 8.75 (d, 1H).

Example 71

Preparation of 3-cyanomethyl-5-fluoro-2-methyl-7-[4-fluorophenacyl)pyrrolo[2,3-b]pyridine hydrochloride A mixture of 3-(cyanomethyl)-5-fluoro-2-methylpyrrolo[2,3-b]pyridine (10mg, 0.053 mmol) and 4-fluorophenacyl chloride (19 mg, 0.11 mmol) in acetonitrile (0.2 ml) was refluxed under argon for 26 h, during which time the initial solution was transformed into a suspension. Then the suspension was allowed to reach room temperature, diluted with diethyl ether (2ml), and filtered. The crystalline product was washed with diethyl ether to give 8 mg (42%) of the title compound.

($^1$H-NMR, 500 MHz, CD$_3$OD) 8.77 (dd, 1H, J$_1$ 8 Hz, J$_2$ 2 Hz), 8.66 (m, 1H), 8.23 (m, 2H), 7.39 (t, 1H, J 8.5 Hz), 6.47 (s, 2H), 4.12 (s, 2H), 2.57 (s, 3H).

Example 72

Preparation of 3-cyanomethyl-5-fluoro-2-methyl-7-((2,4-difluorophenacyl)phenacyl)pyrrolo[2,3-b]pyridine hydrochloride The title compound was prepared from 3-(cyanomethyl)-5-fluoro-2-methylpyrrolo[2,3-b]pyridine (10 mg, 0.053 mmol) and 2,4-difluorophenacyl chloride (128 mg, 0.67 mmol) in acetonitrile (0.2 ml) in the same fashion as described in example 71; yield 16 mg (80%).

($^1$H-NMR, 500 MHz, CD$_3$OD) 8.77 (dd, 1H, J$_1$ 7.5Hz, J$_2$ 1.5Hz), 8.65 (m, 1H), 8.16 (m, 1H), 8.07 (m, 1H), 7.33 (m, 1H), 7.23 (m, 1H), 6.32 (s, 2H), 4.12 (s, 2H), 2.57 (s, 3H).

Example 73

Preparation of 3-cyanomethyl-5-fluoro-2-methyl-7-(2-methoxyphenacyl)pyrrolo[2,3-b]pyridine hydrobromide A mixture of 3-(cyanomethyl)-5-fluoro-2-methylpyrrolo[2,3-b]pyridine (20 mg, 0.11 mmol) and 2-methoxyphenacyl bromide (30 mg, 0.13 mmol) in acetonitrile (0.2 ml) was refluxed under argon for 6 h, during which time the initial solution was transformed into a suspension. Then the suspension was allowed to reach room temperature, diluted with diethyl ether (2 ml), filtered, and washed with diethylether to give 36 mg (81%) of the title compound.

($^1$H-NMR, 500 MHz, CD$_3$OD) 8.74 (dd, 1H, J$_1$ 8 Hz, J$_2$ 2 Hz,), 8.68 (m, 1H), 8.00 (dd, 1H, J$_1$ 8 Hz J$_2$ 2 Hz), 7.73 (m, 1H), 7.34 (d, 1H, J 8 Hz), 7.12 (t, 1H, J 7.5 Hz), 6.29 (s, 2H), 4.15 (s, 3H), 4.12 (s, 2H), 2.56 (s, 3H).

Example 74

Preparation of 3-cyanomethyl-5-fluoro-2-methyl-7-(2-hydroxyphenacyl)pyrrolo[2,3-b]pyridine A mixture of 3-cyanomethyl-5-fluoro-2-methyl-7-(2-methoxyphenacyl)pyrrolo[2,3-b]pyridine hydrobromide (25 mg, 0.06 mmol), methylene chloride (2 ml), and BBr$_3$ in methylene chloride (1M; 0.4 ml) under argon was refluxed for 8 h. The red gum was digested in a methylene chloride aqueous sodium bicarbonate mixture. The organic phase was dried over anhydrous Na$_2$SO$_4$, filtered, and evaporated to give a yellow crystalline product. Yield 19 mg (98%).

($^1$H-NMR, 500 MHz, CD$_3$OD) 8.17 (dd, 1H, J$_1$ 8.5 Hz, J$_2$ 2 Hz), 8.09 (m, 1H), 7.98 (dd, 1H, J$_1$ 8 Hz, J$_2$ 1.5 Hz), 7.57 (m, 1H), 7.02 (m, 2H), 3.96 (s, 2H), 3.34 (s, 2H), 2.46 (s, 3H).

The following Table 1 gives illustrative examples of compounds of the invention

TABLE 1

Illustrative compounds of the invention

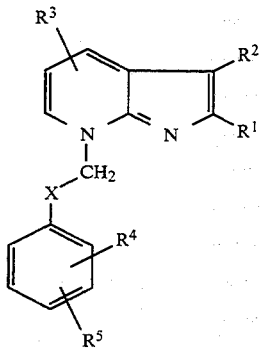

| Example No. | X | R$^1$ | R$^2$ | R$^3$ | R$^4$ | R$^5$ | Yield % |
|---|---|---|---|---|---|---|---|
| 1 | CH$_2$ | CH$_3$ | H | H | H | H | 62 |
| 2 | CH$_2$ | CH$_3$ | Cl | H | H | H | 50 |
| 3 | CH$_2$ | CH$_3$ | CH$_2$CN | H | H | H | 25 |
| 4 | CH$_2$ | H | CH$_3$ | H | H | H | 27 |
| 5 | CH$_2$ | CH$_2$OH | CH$_3$ | H | H | H | 13 |
| 6 | CH$_2$ | Cl | CH$_3$ | H | H | H | 18 |
| 7 | CH$_2$ | CH$_3$ | CH$_3$ | 6-NH$_2$ | H | H | 6 |
| 8 | C=O | CH$_3$ | CH$_3$ | H | H | H | 69 |
| 9 | C=O | CH$_3$ | Cl | H | H | H | 67 |
| 10 | C=O | CH$_3$ | CH$_3$ | H | 4'-Br | H | 92 |
| 11 | CHOH | CH$_3$ | CH$_3$ | H | H | H | 94 |
| 12 | CHOH | CH$_3$ | Cl | H | H | H | 19 |
| 13 | CHOH | CH$_3$ | CH$_3$ | H | 4'-CN | H | 61 |
| 14 | C=O | CH$_3$ | H | H | H | H | 88 |
| 15 | C=O | CH$_3$ | CH$_3$ | H | 2'-CF$_3$ | H | 36 |
| 16 | C=O | CH$_3$ | Br | H | H | H | 37 |
| 17 | C=O | Cl | CH$_3$ | H | H | H | 65 |
| 18 | CHOH | Cl | CH$_3$ | H | H | H | 84 |
| 19 | C=O | CH$_3$ | OCH$_3$ | H | H | H | 34 |
| 20 | C=O | CH$_2$OCH$_3$ | CH$_3$ | H | H | H | 20 |
| 21 | C=O | Cl | CH$_3$ | H | 4'-F | H | 57 |
| 22 | CHOH | Cl | CH$_3$ | H | 4'-F | H | 99 |
| 23 | C=O | Cl | CH$_2$CN | H | H | H | 9 |
| 24 | C=O | CH$_3$ | CH$_3$ | H | 2'-SCH$_3$ | H | 20 |
| 25 | C=O | CH$_3$ | HO | H | H | H | 23 |
| 26 | C=O | CH$_3$ | CH$_3$ | 5-CF$_3$ | H | H | 15 |

TABLE 1-continued

Illustrative compounds of the invention

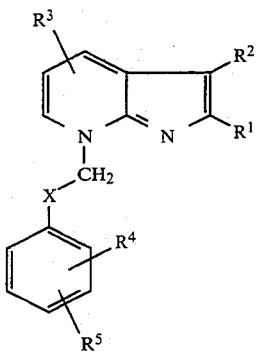

| Example No. | X | R1 | R² | R³ | R⁴ | R⁵ | Yield % |
|---|---|---|---|---|---|---|---|
| 27 | C=O | CH₃ | CH₃ | H | 4'-CN | H | 85 |
| 28 | C=O | CH₃ | CH₃ | H | 4'-F | H | 64 |
| 29 | C=O | CH₃ | CH₃ | H | 4'-OCH₃ | H | 73 |
| 30 | C=O | CH₃ | CH₃ | H | 3'-OCH₃ | H | 70 |
| 31 | C=O | CH₃ | CH₃ | H | 2'-OCH₃ | H | 71 |
| 32 | C=O | CH₃ | CH₃ | H | 2'-F | 4'-F | 56 |
| 33 | C=O | CH₃ | CH₂CN | 5-Cl | H | H | 91 |
| 34 | CHOCH₃ | CH₃ | CH₃ | H | H | H | 65 |
| 35 | C=O | CH₃ | CH₃ | H | 2'-NO₂ | H | 66 |
| 36 | C=O | CH₃ | CH₃ | H | 2'-NH₂ | H | 46 |
| 37 | C=O | CH₃ | CH₃ | H | 4'-CH₃ | H | 74 |
| 38 | CHOH | CH₃ | CH₃ | H | H | H | 92 |
| 39 | CHOH | CH₃ | CH₃ | H | H | H | 82 |
| 40 | C=O | CH₃ | CH₃ | H | 2'-OH | H | 62 |
| 41 | CH₂ | CH₃ | CH₃ | 6-SCH₃ | H | H | 13 |
| 42 | CH₂ | CH₃ | CH₃ | 6-SCH₂CH₂C₆H₅ | H | H | 26 |
| 43 | C=O | CH₃ | CH₃ | 6-SCH₃ | H | H | 35 |
| 44 | C=O | CH₃ | CH₃ | 5-SCH₃ | H | H | 63 |
| 45 | C=O | CH₃ | CH₃ | 5-SOCH₃ | H | H | 41 |
| 46 | CH₂ | CH₃ | CH₃ | H | 2'-COOH | H | 23 |
| 47 | C=O | CH₃ | CH₃ | 5-Br | H | H | 72 |
| 48 | C=O | CH₃ | CH₃ | 5-CN | H | H | 26 |
| 49 | C=O | CH₃ | CH₂CN | H | H | H | 58 |
| 50 | C=O | CH₃ | CH₂—N(N=)pyrazolyl | H | H | H | 39 |
| 51 | C=O | CH3 | CH₂CN | H | 4'-F | H | 55 |
| 52 | CH₂ | CH₃ | CH₃ | H | 2'-NHCOCH₃ | H | 8 |
| 53 | C=O | CH₃ | CH₃ | H | 2'-F | 6'-F | 54 |
| 54 | C=O | CH₃ | SCN | H | H | H | 23 |
| 55 | C=O | 4-Br-C₆H₄— | CH₃ | H | H | H | 74 |
| 56 | C=O | 4-(CH₃OOC)-C₆H₄— | CH₃ | H | H | H | 46 |
| 57 | C=O | 4-((CH₃)₂CHOOC)-C₆H₄— | CH₃ | H | H | H | 30 |
| 58 | C=O | C₆H₅— | CH₃ | H | H | H | 97 |

TABLE 1-continued

Illustrative compounds of the invention

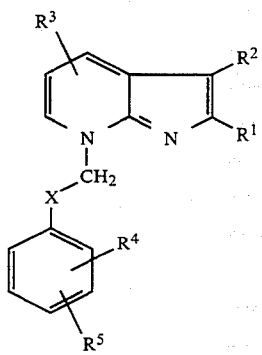

| Example No. | X | R1 | R2 | R3 | R4 | R5 | Yield % |
|---|---|---|---|---|---|---|---|
| 59 | C=O | -⌬-CH₃ | CH₃ | H | H | H | 96 |
| 60 | C=O | -⌬-OCH₃ | CH₃ | H | H | H | 92 |
| 61 | | | | | | | |
| isom1 | C=NOCH₃ | CH₃ | CH₃ | H | H | H | 60 |
| isom2 | C=NOCH₃ | CH₃ | CH₃ | H | H | H | 21 |
| 62 | CHOH | Cl | CH₂CN | H | H | H | 46 |
| 63 | C=O | CH₃ | CH₂CN | 5-F | H | H | 90 |
| 64 | C=O | -⌬ | CH₃ | 5-Br | H | H | 73 |
| 65 | C=O | -⌬ | CH₂CN | H | H | H | 70 |
| 66 | C=O | -⌬ | CH₂CONH₂ | H | H | H | 22 |
| 67 | CHOH | CH₃ | CH₂CN | 5-Cl | H | H | 42 |
| 68 | C=O | CH₃ | CH₂CN | H | 2'-F | 4'-F | 68 |
| 69 | C=O | CH₃ | CH₂CN | H | 2'-OCH₃ | H | 54 |
| 70 | C=O | CH₃ | CH₂CN | H | 2'-OH | H | 73 |
| 71 | C=O | CH₃ | CH₂CN | 5-F | 4'-F | H | 42 |
| 72 | C=O | CH₃ | CH₂CN | 5-F | 2'-F | 4'-F | 80 |
| 73 | C=O | CH₃ | CH₂CN | 5-F | 2'-OCH₃ | H | 81 |
| 74 | C=O | CH₃ | CH₂CN | 5-F | 2'-OH | H | 98 |
| 75 | CHOH | Cl | CH₂CN | 5-OH | H | H | |
| 76 | C=O | Cl | CH₃ | 5-F | H | H | |
| 77 | C=O | Cl | CH₃ | 5-F | 2'-F | 4'-F | |
| 78 | C=O | Cl | CH₃ | 5-OCH₃ | H | H | |
| 79 | CHOH | Cl | CH₃ | 5-OH | 2'-F | 4'-F | |
| 80 | C=O | Cl | CH₃ | 6-CH₂OCH₃ | H | H | |
| 81 | CHOH | Cl | CH₃ | 6-NH₂ | H | H | |
| 82 | C=O | Cl | CH₃ | 6-NHCOCH₃ | H | H | |
| 83 | C=O | Cl | CH₂OH | H | H | H | |
| 84 | C=O | CH₃ | CF₃ | H | H | H | |
| 85 | CHOH | Cl | CH₂C CH | H | H | H | |
| 86 | C=O | CH₃ | CH₂CN | 5-OCH₃ | H | H | |
| 87 | C=O | CH₃ | NH₂ | 5-F | H | H | |
| 88 | CHOH | Cl | CH₃ | 5-OCH₃ | H | H | |
| 89 | CHOH | Cl | CH₃ | 5-F | H | H | |
| 90 | CHOH | CH₃ | CH₂CN | 5-F | H | H | |
| 91 | CHOH | CH₃ | CH₂CN | 5-F | 4'-F | H | |

TABLE 1-continued

Illustrative compounds of the invention

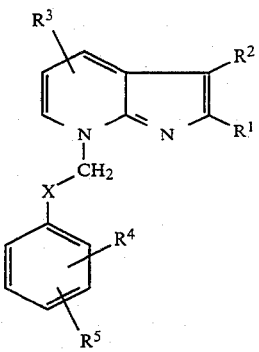

| Example No. | X | R1 | R2 | R3 | R4 | R5 | Yield % |
|---|---|---|---|---|---|---|---|
| 92 | CHOH | CH₃ | CH₂CN | 5-F | 2'-OCH₃ | H | |
| 93 | CHOH | CH₃ | CH₂CN | 5-F | 2'-OH | H | |
| 94 | CHOH | CH₃ | CH₂CN | 5-F | 2'-F | 4'-F | |
| 95 | CH₂ | CH₃ | CH₂CN | 5-F | 2'-OCH₃ | H | |
| 96 | CH₂ | CH₃ | CH₂CN | 5-F | 2'-OH | H | |
| 97 | CH₂ | CH₃ | CH₂CN | 5-F | 2'-F | 4'-F | |
| 98 | CH₂ | CH₃ | CH₂CN | 5-F | 4'-F | H | |
| 99 | CH₂ | CH₃ | CH₂CN | 5-F | H | H | |
| 100 | CHOCH₃ | CH₃ | CH₂CN | 5-F | H | H | |
| 101 | CHOCH₃ | CH₃ | CH₂CN | 5-F | 2'-F | 4'-F | |
| 102 | CHOCH₃ | CH₃ | CH₂CN | 5-F | 4'-F | H | |
| 103 | CHOCH₃ | CH₃ | CH₂CN | 5-F | 2'-OCH₃ | H | |
| 104 | CHOCH₃ | CH₃ | CH₂CN | 5-F | 2'-OH | H | |

The following examples illustrate intermediates useful in the preparation of compounds exemplified in the examples

Example I

Preparation of 3-[(dimethylamino)methyl]-2-methyl-pyrrolo[2,3-b]pyridine

A solution of 200 mg (1.5 mmol) 2-methyl-pyrrolo[2,3-b]pyridine 200 mg (2.5 mmol) dimethylaminhydrochloride and 73 mg (2.5 mmol) paraformaldehyde in 2,5 ml methanol was refluxed for four days. The reaction mixture was cooled to room temperature and the solvent was evaporated under reduced pressure. To the residue was added 2 ml water and ml methylene chloride and the pH was adjusted to 11 with 2 M sodium hydroxide. The organic layer was washed once with water dried over sodium sulfate and the solvent was evaporated to give 0.17 g (60%) of title compound.

($^1$H-NMR, 500 MHz, CDCl₃). 2.25(s,6H), 2.50(s,3H), 3.55(s,2H), 7.03(dd, 1H), 7.92 (d, 1H), 8.01/dd, 1H).

Example II

Preparation of 3-[(trimethylamino)methyl]pyrrolo[2,3-b]pyridine.

A solution of 163 mg (0.86 mmol) of Example I and 135 mg (0.95 mmol) of methyliodide in 1 ml ethanol were stirred for 40 hours at room temperature. The solvent was evaporated and the crude product 270 mg (95%) was used directly in the next step.

($^1$H-NMR, 500 MHz, DMSO-d₆). 3.10(s,9H), 3.30(s,3H), 4.62(s,2H), 7.12(dd, 1H), 8.08(d, 1H), 8.19(d, 1H).

Example III

Preparation of 3-cyanomethyl-2-methylpyrrolo[2,3-b]pyridine

To a solution of 270 mg (0.82 mmol) of Example II in 2,5 ml dimethylformamide was added 44 mg (0.90) mmol of sodium cyanide and heated at 100° C. for 1.5 hours with stirring the reaction mixture was cooled to room temperature and partitioned between water and methylene chloride. The organic layer was dried over sodium sulfate and the solvent was evaporated to give 130 mg (98%) of the title compound.

($^1$H-NMR, 500 MHz, CDCl₃). 2.53(s,3H), 3.77(s,2H), 7.12(dd, 1H), 7.92(dd, 1H), 8.27(dd, 1H).

Example IV

Preparation of 3-chloro-2-methylpyrrolo[2,3-b]pyridine

To a solution of 0,7 g (5.3 mmol) of 2-methylpyrrolo[2,3-b]pyridine in 2,5 ml glacial acetic acid was added dropwise 0,8 g (5.9 mmol) of sulfuryl chloride at room temperature and with stirring. The reaction mixture was stirred for 1 hour. The solvent was evaporated and the residue was partitioned between methylene chloride and a saturated sodium bicarbonate solution. The organic layer was dried over sodium sulfate and the solvent was evaporated. The residue was crystallized from ether: ethyl acetate, 5:1 to give 0,45 g (51%) of the title compound.

($^1$H-NMR, 500 MHz, CDCl₃). 2.50(s,3H), 7.12(dd, 1H), 7.84 (dd, 1H), 8.25(dd, 1H).

Example V

Preparation of 2-hydroxymethyl-3-methylpyrrolo[2,3-b]pyridine 2,3-dimethylpyrrolo[2,3-b]pyridine(0,2 g 0.0014 mol) was treated in 3 ml acetic acid with an equimolecular amount of bromine and after 5 min yellow precipitate was formed. The solid was filtered off and treated with 3 ml water for 60 min. The mixture was made alkaline with bicarbonate and extracted with methylene chloride. When the organic layer had been dried and evaporated the product was isolated as a yellow oil. (0,12 g, 53%).

($^1$H-NMR, 300 MHz, CDCl$_3$). 2.2(s,3H), 4.7(s,2H), 7.0(dd, 1H), 7.8(dd, 1H), 8.25(dd, 1H).

Example VI

Preparation of 2-chloro-3-methylpyrrolo[2,3-b]pyridine 3-methylpyrrolo[2,3-b]pyridine (0,5 g 0.0038 mol) was treated in 2 ml acetic acid with an equimolecular amount of sulfuryl chloride at 0° C. for 5 min. The mixture was allowed to warm to room temperature and was stirred for 5 min. After evaporation the residue was dissolved in methylene chloride and was treated with bicarbonate. The organic layer was separated, dried and removed under reduced pressure. Chromatography on silica gel eluting with ethyl acetate gave the desired product. (0,18 g 29%).

($^1$H-NMR, 300 MHz, CDCl$_3$). 2.25(s,3H), 7.05(dd,1H), 7.75(dd,1H), 8.25(dd, 1H).

Example VII

Preparation of 2,3-dimethyl-5-trifluoromethylpyrrolo[2,3-b]pyridine

A mixture of 2-chloro-5-trifluoromethylpyridine (10 g 0.055 mol) and hydrazine mono hydrate (2,7 g, 0.055 mol) in 35 ml n-propanol was refluxed for 2 h and was then stirred 20 h at RT. To the solution was added 4,35 g (0.06 mol) methylethylketon and the mixture was refluxed for 30 min. After the solvent was removed under reduced pressure the residue was partitioned between methylene chloride and bicarbonate solution. The organic layer was dried over Na$_2$SO$_4$ and evaporated. The residue was solved in 80 ml diethylene glycol and refluxed for 5 h. The reaction mixture was poured into ice-water and extracted with methylene chloride. The organic layer was separated dried over Na$_2$SO$_4$ and evaporated. The residue was treated with warm petroleumether ( 60-80 ) wich was decantated and evaporated chromatography twice on silica gel with 1 methylene chloride/methanol 2 ethyl acetate, gave the desired product. ( 0,2 g 1.7% ).

($^1$H-NMR, 300 MHz, CDCl$_3$). 2.3(s,3H), 2.45(s,3H), 8.0(s,1H), 8.5 (s, 1H).

Example VIII

Preparation of 3-methoxy-2-methylpyrrolo[2,3-b]pyridine.

A solution of 7,4 g (68 mmol) 2-hydrazinopyridine and 6,0 g (68 mmol) methoxyaceton in 50 ml of ethanol was refluxed for 1 h. The solvent was removed under reduced pressure. The resulting oil was dissolved in diethylene glycol and refluxed for 1,5 h. The mixture was allowed to cool and was poured into ice-water. Extraction with methylene chloride gave an black oily residue which was treated with boiling petroleumether (60-80). After decanting the solvent was allowed to cool and the precipitated product filtered of affording 4,5 g (41%) pure title compound as a yellow solid.

($^1$H-NMR, 300 MHz, CDCl$_3$). 2.45(s,3H), 3.9(s,3H), 7.0(t,1H), 7.85 (d, 1H), 8.15 (d, 1H).

Example IX

2-Chloro-3-cyanomethylpyrrolo[2,3-b]pyridine.

3-cyanomethylpyrrolo[2,3-b]pyridine (1,55 g, 0.098 mol) was treated in 5 ml acetic acid with an equimolecular amount of sulfurylchloride at 0° C. for 5 min. The mixture was allowed to warm to room temperature and was stirred 5 min. After evaporation the residue was dissolved in methylen chloride and was treated with bicarbonate. The organic layer was separated, dried over Na$_2$SO$_4$ and the solvent was removed under reduced pressure. Chromatography on silica gel eluting with ethyl acetate gave the desired product. (0,4 g 21%).

($^1$H-NMR, 500 MHz, CDCl$_3$). 3.85(s,2H), 7.2(t,1H), 8.05(d, 1H), 8.4(d, 1H).

Example X

2-Methoxymethyl-3-methylpyrrolo[2,3-b]pyridine.

2,3-dimethylpyrrolo[2,3-b]pyridine 0,5 g (0.0034 mol) was treated in 7 ml acetic acid with an equimolecular amount of bromine and after 5 min a yellow precipitate was formed. The solid was filtered off and treated with 20 ml methanol. The mixture was refluxed for 30 min. and was then evaporated. The residue was partitioned between methylene chloride and bicarbonate solution. The organic layer was separated dried over Na$_2$SO$_4$ and evaporated. The residue was treated with boiling petroleumether (60-80) which was decanted and allowed to cool. The precipitated product was filtered off affording 0,13 g (22%) as white solid.

($^1$H-NMR 300 MHz CDCl$_3$). 2.3(s,3H), 3.4(s,3H), 4.65(s,2H), 7.05(dd, 1H), 7.85(d, 1H), 8.3(d, 1H).

Example XI

Preparation of 6-bromo-2,3-dimethyl-pyrrolo[2,3-b]pyridine

A mixture of 2,6-dibromopyridine (47.4 g, 0.3 mol) and hydrazine mono hydrate (97.2 ml, 2.0 mol) in 400 ml propanol was refluxed for 19 h. The solvent was evaporated and the residue taken up in 1000 ml CH$_2$Cl$_2$. The organic layer was washed with 500 ml 5% Na$_2$CO$_3$ (reextraction with 500+250+250 ml CH$_2$Cl$_2$), dried over MgSO$_4$, and evaporated. The residue was recrystallized from 100 ml abs. EtOH leaving 30.0 g 2-bromo-6-hydrazinopyridine. Reprocessing of the mother liquor gave additional 2.5 g. Yield 32,5 g (87%).

A suspension of 2-bromo-6-hydrazinopyridine (32,5 g, 0.17 mol) in abs EtOH was treated with ethyl methyl ketone (20 ml, 0.22 mol) for 1 h at reflux. The reaction mixture was allowed to cool and treated with additional ethyl methyl ketone (10+3+1 ml) until all starting material had dissapeared according to TLC. The reaction mixture was taken up in 150 ml diethylene glycol and the EtOH evaporated at reduced pressure at 70° C. The remaining solution was deaerated and heated to reflux for 22h. The reaction mixture was cooled and paritioned between 1250 ml CH$_2$Cl$_2$ and 1000 ml 2M HCl (reextracted with 250 ml CH$_2$Cl$_2$). The organic layer was washed with further 500 ml 2M HCl and 500 ml H$_2$O dried over MgSO$_4$, and evaporated. Chromatography (silica, CH$_2$Cl$_2$/diethyl ether; 95/5) afforded 6 g 6-bromo-2,3-dimethyl-pyrrolo[2,3-b]pyridine. Recrystallization from 120 ml abs EtOH gave 4,2 g (11%).

($^1$H-NMR, 500 MHz, CDCl$_3$) 2.19(s,3H), 2.42(s,3H), 7.16(d, 1H), 7.59(d, 1H), 9.12(b, 1H).

Example XII

Preparation of 2,3-dimethyl-6-methylthiopyrrolo[2,3-b]pyridine

A deaerated solution of 6-bromo-2,3-dimethyl-pyrrolo [2,3-b]pyridine (225 mg, 1.0 mmol) in 25 ml dry THF was cooled to −78° C. and treated with 1.6M n-BuLi in hexane (1,5 ml, 2.4 mmol). The reaction mixture was brought to 0° C. and the lithiate trapped with dimethyl disulfide (444 μl, 5 mmol). After reacting for 5 min 1.5 ml H$_2$O was added and the THF evaporated. The residue was taken up in 100 ml CH$_2$Cl$_2$ and washed with 50 ml 5% NaHCO$_3$, 50 ml 2M HCl (reextracted twice with 25 ml CH$_2$Cl$_2$), and 50 ml 5% NaHCO$_3$. The organic layer was dried over MgSO$_4$ and evaporated leaving 160 mg (83%) pure 2,3-dimethyl-6-methylthio-pyrrolo[2,3-b]pyridine.

($^1$H-NMR, 500 MHz, CDCl$_3$) 2.17(d,3H), 2.36(s,3H), 2.60(s,3H), 6.94(d,1H), 7.58(d,1H), 8.42(b,1H).

Example XIII

Preparation of 3-thiocyano-2-methylpyrrolo[2,3-b]pyridine

To a solution of 300 mg (2.36 mmol) of 2-methylpyrrolo[2,3-b]pyridine and 920 mg (11.3 mmol) of sodium thiocyanate in 5 ml acetic acid was added 450 mg (2.8 mmol) bromine in 1 ml acetic acid at 5° C. The reaction mixture was stirred for 30 min at 5° C. and thereafter for 16 h at room temperature. The solid was filtered off. To the filtrate was added 20 ml water. The precipitated product was filtered off and washed with water giving 160 mg (37%) of the title compound.

($^1$H-NMR 300 MHz DMSO-d$_6$). 2.55(s,3H), 7.22(dd, 1H), 7.97(dd, 1H), 8.28(dd, 1H), 12.5(s,1H).

Example XIV

Preparation of 3-(1-pyrazolo)methyl-2-methypyrrolo[2,3 -b]pyridine

To a solution of 95 mg (0.29 mmol) of 3[(trimethylammo-nio)-methyl]-pyrrolo[2,3-b]pyridine in 1,0 ml dimethylformamide was added 24 mg (0.35 mmol) of pyrazole and heated at 100° C. for 1.5 hours with stirring. The reaction mixture was cooled to room temperature and partitioned between water and methylene chloride. The organic layer was dried over sodium sulfate and the solvent was evaporated to give 30 mg (48%) of the title compound.

$^1$H NMR (300 MHz, CDCl$_3$). 2.55(s,3H), 5.45(s,2H), 6.20(m,1H), 7.03(m,1H), 7.52(m,1H), 7.62(d,1H), 7.7(m,1H), 8.21(m,1H).

Example XV

5-Cyano-2,3-dimethyl-pyrrolo[2,3-b]pyridine

An autoclave was charged with 5-bromo-2,3-dimethyl-pyrrolo[2,3-b]pyridine (prepared in a similar manner as 6-bromo-2,3-dimethyl-pyrrolo[2,3-b]pyridine (247 mg, 1.1 mmol) and CuCN (135 mg. 1.5 mmol). The mixture was covered with pyridine and heated to 220° C. for 12 h. After cooling the raction mixture was poured into a mixture of FeCl$_3$ hexahydrate (0.9 g), conc HCl (0.5 ml), and water (10 ml). The mixture was heated to 80° C. for 1 h and extracted with CH$_2$Cl$_2$. The organic layer was washed four times with 2M HCl, dried over MgSO$_4$ and evaporated leaving 77 mg (40%) 5-cyano-2,3-dimethyl-pyrrolo[2,3-b]pyridine.

($^1$H-NMR, 300 MHz, DMSO-d$_6$) 2.18(s,3H), 2.35(s,3H), 8.32 (d, 1H), 8.45(d, 1H).

Example XVI

5-Chloro-3-cyanomethyl-2-methyl-pyrrolo[2,3-b]pyridine

A mixture of 2,5-dichloropyridine (10.7 g, 0.07 mol) and hydrazine mono hydrate (34.0 ml, 0.7 mol) in 140 ml propanol was refluxed for 17h. The solvent was evaporated and the residue taken up in 500 ml CH$_2$Cl$_2$. The organic layer was washed with 200 ml 5% NaHCO$_3$ (reextraction with 100 ml CH$_2$Cl$_2$), dried over MgSO$_4$, and evaporated. The residue was recrystallized from 17 ml abs. EtOH leaving 4.7 g 5-chloro-2-hydrazinopyridine. Reprocessing of the mother liquor gave additional 0.1 g. Yield 4.8 g (48%). A mixture of 5-chloro-2-hydrazinopyridine (4.9 g, 34 mmol) and α-(methylthio)acetone (3.5 g, 34 mmol) in 10 ml abs EtOH was heated to reflux. The reaction mixture was allowed to cool and taken up in 30 ml diethylene glycol. The EtOH was evaporated at reduced pressure at 70° C. and the remaining solution deaerated and heated to reflux for 1.5h. The reaction mixture was cooled and taken up in 500 ml CH$_2$Cl$_2$. The organic layer was washed twice with 400 ml H$_2$O (each portion was reextracted with 100 ml CH$_2$Cl$_2$), dried over MgSO$_4$, and evaporated. The residue was filtered through silica eluting with CH$_2$Cl$_2$. Fractions containing product were pooled, a small volume of abs EtOH was added, and the CH$_2$Cl$_2$ evaporated. The precipitated 5-chloro-2-methyl-3-methylthio-pyrrolo[2,3-b]pyridine was collected and washed with a small volume of ligroine affording 1.5 g (20%) pure product. Reprocessing of the mother liquour gave additonal material, 1.0 g (14%).

A deaerated solution of 5-chloro-2-methyl-3-methylthiopyrrolo[2,3-b]pyridine (1.1 g, 5.0 mmol) in 45 ml 1,4-dioxane was heatet to 70° C. and treated with small portions of Raney-Ni until all starting material had disappeared according to GC-MS,(total reaction time: 48h). The catalyst was filtered off and washed with several portions of 5% Na$_2$CO$_3$. Pure 5-chloro-2-methyl-pyrrolo[2,3-b]pyridine appeared as a white precipitate in the filtrate and was collected. A second lot was obtained after evaporating the filtrate, dissolving it in 2M HCl, and carefully basifying the solution with Na$_2$CO$_3$. Yield 0.6 g (74%).

A mixture of 5-chloro-2-methyl-pyrrolo[2,3-b]pyridine (514 mg, 3.1 mmol), paraformaldehyde (102 mg, 3.4 mmol), and dimethylamonium hydrochloride (277 mg, 3.4 mmol), in 12 ml butanol was refluxed for 1.5h. Most of the solvent was evaporated and the remaining moist residue treated with ice cold diethyl ether. The precipitate was collected and dried leaving 707 mg (93%) of a 1:1 mixture of 5-chloro-3-dimethylaminomethyl-2-methyl-pyrrolo[2,3-b]pyridine and the corresponding hydrochloride.

A 1:1 mixture of 5-chloro-3-dimethylaminomethyl-2methylpyrrolo[2,3-b]pyridine and the corresponding hydrochloride (674 mg, 140 mmol) and conc HCl (1.16 ml, 140 mmol) each 12 h until all starting material had disappeared according to DI-MS. The reaction mixture was taken up in 200 ml 5% Na$_2$CO$_3$ and extracted twice with 200 ml CH$_2$Cl$_2$. The combined organic layers were dried over MgSO$_4$ and evaporated leaving 147 mg (26%) pure 5-chloro-3-cyanomethyl-2-methyl-pyrrolo[2,3-b]pyridine.

($^1$H-NMR, 500 MHz, CDCl$_3$) 2.51(s,3H), 3.72(s,2H), 7.87(d,1H), 8.21(d,1H), 9.16(b,1H).

Example XVII 2-(p-Bromophenyl)-3-methyl-pyrrolo[2,3-b]pyridine

A mixture of 2-hydrazinopyridine (11.1 g, 0.10 mol) and p-bromopropiophenone (25 g, 0.12 mol) in 85 ml 95% EtOH was refluxed for 12 h. Evaporation of the solvent afforded a quantitative yield of the corresponding hydrazone. (DI-ms, EI at 70 ev) m/z 303 (5), 274 (70), 183 (100), 155 (65).

The residue was dissolved in 100 ml DEG, deaerated and violently refluxed in a nitrogen atmosphere for 6 h. The reaction mixture was allowed to cool and poured into 700 ml H$_2$O. The precipitated product was collected and recrystallized from EtOH affording 6.48 g (22%) of the desired product.

($^1$H-NMR, 300 MHz, CDCl$_3$). 2.45 (s, 3H), 7.10 (dd, 1H), 7.50 (d, 2H), 7.65 (d, 2H), 7.90 (dd, 1H), 8.25 (d, 1H).

Example XVIII 2-(p-Carboxyphenyl)-3-methyl-pyrrolo[2,3-b]pyridine 2-(p-Bromophenyl)-3-methyl-pyrrolo-[2,3 -b]pyridine (1 g, 3.5 mmol) was dissolved in 200 ml dry THF, deaerated and cooled to −78° C. n-Butyllithium (5.19 ml, 8.4 mmol) was added dropwise and the mixture was allowed to reach room temperature CO$_2$ (g) was bubbled through the solution for 10 min.

Excess of n-butyllithium was destroyed with a small amount of water. The solvent was evaporated and the residue partitioned between 100 ml CH$_2$Cl$_2$ and 100 ml 5% Na$_2$CO$_3$. The water layer was acidified (pH 2) with 2M HCl. The precipitated product was filtered off and dried affording 0.38 g (44%) of the title compound.

($^1$H-NMR, 300 MHz, D$_2$O). 2.35 (s, 3H), 7.15 (bs, 1H), 7.65 (d, 2H), 7.95 (m, 3H), 8.20 (bs, 1H).

Example XIX p-[3methyl-pyrrolo[2,3-b]-pyridine-2]yl-benzoylchloride 2-(p-Carboxyphenyl)-3-methyl-pyrrolo-[2,3b]pyridine (1 g, 4 mmol) was dissolved in 20 ml thionyl chloride at 0° C. The solution was allowed to react at room temperature for 2 h. The solvent was evaporated. The residue was evaporated twice with CH$_2$Cl$_2$ to remove excess of thionyl chloride to give quantitative yield of the title compound.

($^1$H-NMR, 300 MHz, CDCl$_3$). 2.50 (s, 3H), 7.40 (t, 1H), 7.80 (d, 2H), 8.20 (m, 3H), 8.40 (d, 1H).

Example XX methyl-[p-(3-methyl-pyrrolo[2,3-b]-pyridine)-2]yl benzoate p-[3-methyl-pyrrolo[2,3 -b]-pyridine-2]yl benzoylchloride (0.41 g, 1.5 mmol) was chromatographed on silica gel (CH$_2$Cl$_2$: MeOH, 95:5) to give 0.28 g (69%) of the title compound.

($^1$H-NMR, 300 MHz, CDCl$_3$). 2.50 (s, 3H), 3.95 (s, 3H), 7.10 (dd, 1H), 7.75 (d, 2H), 7.95 (d, 1H), 8.15 (d, 2H), 8.20 (d, 1H).

Example XXI

Isopropyl-[p(3-methyl-pyrrolo[2,3-b]pyridine)-2]yl benzoate p-[3-Methyl-pyrrolo[2,3-b]-pyridine-2]yl benzoylchloride (1.1 g, 4 mmol) was dissolved in 20 ml CH$_2$Cl$_2$. 2-Propanol (1.20, 20 mmol) and triethylamine (0.4 g, 4 mmol) was added and the mixture was allowed to react at room temperature for 24 h. The solvent was evaporated and the residue was purified by chromatography (silica, CH$_2$Cl$_2$:MeOH, 97:3) to give 102 mg (9%) of the title compound.

($^1$H-NMR, 300 MHz, CDCl$_3$). 1.40 (s, 3H), 1.45 (s, 3H), 2.55 (s, 3H), 5.35 (m, 1H), 7.10 (dd, 1H) 7.86 (d, 2H), 7.95 (d, 1H), 8.20 (m, 3H).

Example XXII

3-Methyl-2-phenylpyrrolo[2,3 -b]pyridine

A mixture of 1-hydrazinopyridine (21.8 g, 20 mmol) and propiophenone (29.3 g, 22 mmol) in 160 ml 95% EtOH was refluxed for 3 h. Evaporation of the solvent afforded a quantitative yield of the corresponding hydrazone.

(DI-MS, E1 at 70 eV) m/z 225 (8), 196 (100), 148 (15).

The residue was dissolved in 200 ml DEG, deaerated and violently refluxed in a nitrogen atmosphere for 4 h. The reaction mixture was allowed to cool overnight and poured into 1000 ml H$_2$O. The precipitated product was collected and recrystallized from EtOH affording 18.4 g (44%) of the desired product.

($^1$H-NMR, 500 MHz, CDCl$_3$). 2.49 (s, 3H), 7.07 (dd, 1H), 7.42 (t, 1H), 7.55 (t, 2H), 7.73 (d, 2H), 7.91 (d, 1H), 8.21 (d, 1H), 11.38 (b, 1H).

Example XXIII

3-Methyl-2-(p-methylphenyl)pyrrolo[2,3-b]pyridine

The title compound was prepared on a 10 mmol scale following the procedure described in example XXII above. Yield 0.9 g (4%), (DI-MS, E1 at 70 eV of the hydrazone) m/z 239 (5), 210 (100), 148 (12).

($^1$H-NMR, 500 MHz, CDCl$_3$ of the title compound). 2.45 (s, 3H), 2.47 (s, 3H), 7.08 (dd, 1H), 7.34 (d, 2H), 7.59 (d, 2H), 7.89 (dd, 1H), 8.23 (dd, 1H), 10.6 (b, 1H).

Example XXIV 2-(p-Methoxyphenyl)-3-methyl-pyrrolo[2,3-b]pyridine

The title compound was prepared on a 20 mmol scale following the procedure described in example XXII above. Yield 6.0 g (13%). (DI-MS, E1 at 70 eV of the hydrazone) m/z 255 (8), 226 (100), 211 (12).

($^1$H-NMR, 500 MHz, CDCl$_3$ of the title compound). 2.45 ( s, 3H), 3.90 (s, 3H), 7.06 (m, 3H), 7.63 (d, 2H), 7.87 (dd, 1H), 8.12 (dd, 1H), 10.7 (b, 1H).

Example XXV

Preparation of 5-fluoro-2hydrazinopyridine

A mixture of 2-chloro-5-fluropyridine (5 g, 0.038 mol) and hydrazine monohydrate (15 ml, 0.32 mol) in n-propanol (40 ml) in a teflon container was purged with argon and heated in a stainless steel bomb at 200° C. for 19 h (magnetic stirring). Evaporation of solvent and excess hydrazine monohydrate in vacuo gave a solid residue (5.9 g) which was dissolved in sodium bicarbonate solution (5%) and extracted with 6×50 ml ethyl acetate. The combined extracts were dried over anhydrous Na$_2$SO$_4$, filtered and evaporated to give an oil (2.9 g) which proved difficult to purify and was therefore used as such in the next step. The crude product consisted of a ternary mixture of the desired product, 2-chloro-5-hydrazinopyridine, and 5-hydrazinopyridine.

($^1$H-NMR, 500 MHz, DMSO-d$_6$). 6.73 (dd, 1H, $J_1$ 9 Hz, $J_2$ 3.5 Hz), 7.41 (td, 1H, $J_1$ 9.5 Hz, $J_2$ 3 Hz), 7.95 (d, 1H, $J_1$ 3 Hz)

Example XXVI

Preparation of 5-fluoro-2-methyl-3-methyltiopyrrolo[2,3-b ]pyridine

A solution of crude 5-fluoro-2hydrazinopyridine (6.7 g, max. 0.053 mol) and (α-methyltio)acetone (6.04 g, 0.058 mol) in ethanol (99.5%, 15 ml) was heated to reflux for a couple of minutes and then evaporated under reduced pressure to afford an oil (11.5 g) . A solution of the oil in diethylene glycol (50 ml) was heated at reflux temperature under argon for 8 h. The reaction mixture was cooled to room temperature, diluted with Na$_2$CO$_3$ solution (10%, 200 ml), and extracted with diethyl ether (200 and methylene chloride (2×200 ml). The combined extracts were dried over anhydrous Na$_2$SO$_4$ and evaporated in vacuo to give an oil from which the title compound (0.22 g, 2%, two steps) was isolated by flash chromatography (SiO$_2$/-MeOH:CH$_2$Cl$_2$ 0, 1, and 2%).

MS m/z (relative intensity) 196 (100, M+), 181 (100), 137 (58).

Example XXVII

Preparation of 5-fluoro-2-methylpyrrolo[2,3-b]pyridine

Raney-Ni (10 g wet alloy, Aldrich W2, was washed with 10×50 ml deionized water and 5×40 ml dioxane) was suspended in a solution of 5-fluoro-2-methyl-3-methyltiopyrrolo[2,3-b]pyridine (0.5 g, 2.5 mmol) in dioxane (50 ml). The reaction mixture was stirred under hydrogen for 43 h. More Raney-Ni (5 g wet) was added and stirring under hydrogen was continued over a weekend (69 h). Filtration through Celite and evaporation gave 0.24 g crude product. Additional crude product (0.48 g) was isolated by Soxhlet extraction of the Raney-Ni. The crude prucuct was used in the next step without prior purification.

MS m/z (relative intensity) 150 (75, M+), 149 (100), 122 (15).

Example XXVIII

Preparation of 3-(cyanomethyl)-5-fluoro-2-methylpyrrolo [2 3-b]pyridine

Mannich reagent (0.8 ml, prepared according to Liebigs (1971) Ann. Chem., 743, 95–111) was added under stirring to pre-cooled (−78° C.) 5-fluoro-2-methylpyrrolo[2,3-b]pyridine (0.33 g, 2.2 mmol) under argon. The flask containing the reaction mixture was then placed in an ice bath and stirring was continued to give a white suspension. The ice lumps melted within 2 h and the resulting water bath was allowed attain room temperature. After 24 h almost all suspension had dissolved. The reaction mixture was cooled in an ice bath, diluted with deionized water (8 ml) and extracted with diethyl ether (2×5 ml) to remove some remaining starting material and a by-product (propably the corresponding Mannich dimer). Sodium cyanide (1.08 g, 0.022 mol) was added to the water phase, assumed to contain 3-(dimethylaminomethyl)-5-fluoro-2-methylpyrrolo[2,3-b]pyridine, and the resulting solution was refluxed for 2 h to afford a suspension which was isolated by filtration. Purification by flash chromatography (SiO$_2$/CH$_2$Cl$_2$:MeOH 19:1) gave 0.28 g (67%, two steps) of 3-(cyanomethyl)-5-fluoro-2-methylpyrrolo[2,3-b]pyridine.

MS m/z (relative intensity) 189 (100, M+), 188 (97), 174 (83), 163 (55), 162 (35), 147 (18), 121 (19).

Example XXIX

Preparation of 5-bromo-2-hydrazinopyridine

Starting from 2,5-dibromopyridine the title compound was prepared in the same fashion as 5-chloro-2-hydrazinopyridine. ($^1$H-NMR, 300 MHz, CDCl$_3$). 3.78 (br s, 2H), 5.83 (br s, 1H), 6.65 (d, 1H, J 9 Hz), 7.54 (dd, 1H, J$_1$ 9 Hz, J$_2$ 2.5 Hz), 8.14 (d, 1H, J 2.5).

Example XXX

Preparation of 5-bromo-3-methyl-2-phenylpyrrolo[2.3-b]pyridine

5-Bromo-2-hydrazinopyridine (15.6 g, 0.083 mol) and propiophenone (11.1 ml) was heated at 90° C. (steam bath) for 30 min. Then toluene (100 ml) was added and the resulting solution was refluxed for 2 h to remove water by azeotropic distillation (Dean Stark apparatus). Evaporation of solvent gave 26.4 g of crude product, assumed to be the desired hydrazone. Crude hydrazone (3.02 g) was dissolved in diethylene glycol (30 ml) and heated at 245° C. under argon for 24 h. The reaction mixture was poored crushed ice and extracted with methylene chloride. Drying over MgSO$_4$ and evaporation of solvent left a tary residue which was triturated with diethyl ether to produce 0.84 g (30%) of a brownish, semi-crystalline product.

($^1$H-NMR, 300 MHz, DMSO-d$_6$). 2.50 (s, 3H), 7.41 (t, 1H, J 7 Hz), 7.52 (t, 2H, J 7 Hz), 7.71 (d, 2H, J 7 Hz), 8.23 (m, 2H).

Example XXXI

Preparation of 2-phenylpyrrolo[2,3-b]pyridine

A mixture of acetophenone (28.2 g, 0.24 mol) and 2-hydrazinopyridine (25.7 g, 0.24 mol) was heated on a steam bath for 0.5 h. Toluene (200 ml) was added to give a solution which was refluxed for 2 h to remove water by azeotropic distillation (Dean Stark apparatus). Evaporation of solvent gave 55.4 g of crude product, assumed to be the desired hydrazone. The crude hydrazone was purified by distillation (Vigreux apparatus) to give a yellow oil (38.4 g, 77%). Fresh hydrazone (18 g, 0.085 mol) was dissolved in tetraethylene glycol (180 ml) and refluxed under argon for 6 h. The reaction mixture was cooled, diluted with diethyl ether (250 ml) and water (250 ml) under stirring. The phases were separated and the water phase was reextracted with diethyl ether (200 ml). The combined ether phases were dried over anhydrous sodium sulphate, filtered and evaporated to leave a black oil (14.9 g) which was further purified by kugel-rohr distillation, flash chromatography (SiO$_2$/MeOH:CH$_2$Cl$_2$, first none methanol, then gradually more methanol to increase mobility) and recrystallization (methylene chloride) to afford 1.5 g of pure 2-phenylpyrrolo[2,3 -b]pyridine.

MS m/z (relative intensity) 195 (15, M+1), 194 (100, M+), 193 (20), 166 (12), 139 (10), 97 (21), 91 (18), 84 (11).

Example XXXII

Preparation of 3-(cyanomethyl)-2-phenylpyrrolo[2.3-b]pyridine

Aqueous formaldehyde (36%, 1.7 ml) was cooled (ice bath), then acetic acid (3 ml) and aqueous dimethylamine (40%, 2.5 ml) were added. That solution was kept at 0° C. for 30 minutes before part of it (2.6 ml) was transfered to a precooled (−78° C.) flask containing 2-phenylpyrrolo[2,3-b]pyridine under argon. After 5 min the temperature was changed to 0° C. (ice bath) and it was allowed to reach room temperature within 2 h. Stirring of the resulting suspension was maintained for 110 h. Re-cooling to 0° C. and addition of cooled deionized water (25 ml) and diethyl ether (7 ml) under stirring gave two phases which were separated. The organic phase was discarded since it was assumed to contain some remaining starting material and some Mannich dimer.

Sodium cyanide (3.6 g) was added to the water phase which was assumed to contain 3-(dimethylaminomethyl)-2-phenylpyrrolo [2,3-b]pyridine. The mixture was refluxed for 3 h without any noticeable change in TLC apprearance (SiO$_2$/CH$_2$Cl$_2$:MeOH 19:1), indicating that the Mannich base was unchanged. 3-(Dimethylaminomethyl)-2-phenylpyrrolo[2,3-b]pyridine was recovered from the reaction mixture by the following procedure. Water (25 ml) was added, solid material was filtered off, and filtrate was extracted with methylene chloride. The major part of the Mannich base was isolated from the filter cake by repeated washing with methylene chloride. The combined washings (3×100 ml), containing the sparingly soluble Mannich base, was dried and evaporated until precipitation just started. The saturated solution was loaded on a flash chromatography column ($SiO_2/CH_2Cl_2$, prepared in $CH_2Cl_2$:MeOH 9:1). Recovered 3-(dimethylaminomethyl)-2-phenylpyrrolo[2,3 -b]pyridine (1.26 g, 68%) was isolated by eluting with methylene chloride methanol mixtures (1.500 ml $CH_2Cl_2$; 2.500 ml MeOH:$CH_2Cl_2$ 2:98;3.500 ml MeOH:$CH_2Cl_2$ 4:96;4.500 ml MeOH:$CH_2CL_2$ 8:92).

Ethyl iodide (1.94 g, 0.012 mol) was added to a solution of recovered Mannich base (1.25 g, 5 mmol) in methanol (10 ml). The solution was stirred under argon for 1.5 h. Then a solution of potassium cyanide (0.81 g, 0.012 mol) in deionized water (1.8 ml ) was added. The reaction mixture was heated to reflux for 1 h. Solvents were evaporated and the resulting residue was diluted with water (10 ml) and extracted with ethyl acetate (3×10 ml). The combined extracts were dried ($MgSO_4$) and evaporated in vacuo to give a solid which was purified by flash chromatography ($SiO_2/CH_2Cl_2$, elution with increasing amounts of methanol, se above) leaving pure title compound (0.85 g, 73%).

($^1$H-NMR, 300 MHz, DMSO-$d_6$). 4.18 (s, 2H), 7.17 (q, 1H, $J_1$ 7.5 Hz, $J_2$ 4.5 Hz), 7.43-7.51 (m, 1H), 7.54-7.60 (m, 2H), 7.67-7.71 (m, 2H), 8.14 (dd, 1H, $J_1$ 7.5 Hz, $J_2$ 1.5 Hz), 8.3 0 (dd, 1H, $J_1$ 4.5 Hz, $J_2$ 1.5 Hz).

Example XXXIII

Preparation of 3-(carbamoylmethyl)-2-phenylpyrrolo[2.3-b]pyridine 3-(Cyanomethyl)-2-phenylpyrrolo[2,3-b]pyridine (0.37 g, 1.39 mmol), powdered KOH (0.82 g), and t-butanol (5 ml) were heated to reflux under argon for 3 h. The reaction mixture was then cooled to room temperature and diluted with deionized water (6.5 ml) to give a precipitate. The suspension was extracted with methylene chloride and filtered. The filter cake consisted of pure title compound.

($^1$H-NMR, 300 MHz, DMSO-$d_6$). 3.59 (s, 2H), 6.96-7.03 (m, 2H), 7.33-7.51 (m, 4H), 7.79-7.84 (m, 2H), 8.13 (dd, 1H, $J_1$ 7.5 Hz, $J_2$ 1.5 Hz ), 8.30 ( dd, 1H, $J_1$ 4.5 Hz, $J_2$ 1.5 Hz).

For clinical use the compounds of the invention are formulated into pharmaceutical formulations for oral, rectal, parenteral or other mode of administration. The pharmaceutical formulation contains a compound of the invention in combination with a pharmaceutically acceptable carrier. The carrier may be in the form of a solid, semi-solid or liquid diluent, or a capsule. These pharmaceutical preparations are a further object of the invention. Usually the amount of active compounds is between 0.1–95% by weight of the preparation, between 0.2–20% by weight in preparations for parenteral use and between 1 and 50% by weight in preparations for oral administration. In the preparation of pharmaceutical formulations containing a compound of the present invention in the form of dosage units for oral administration the compound selected may be mixed with a solid, powdered carrier, such as lactose, saccharose, sorbitol, mannitol, starch, amylopectin, cellulose derivatives, gelatin, or another suitable carrier, as well as with lubricating agents such as magnesium stearate, calcium stearate, sodium steryl fumarate and polyethylene glycol waxes. The mixture is then processed into granules or pressed into tablets. Soft gelatine capsules may be prepared with capsules containing a mixture of the active compound or compounds of the invention, vegetable oil, fat, or other suitable vehicle for soft gelatine capsules. Hard gelatine capsules may contain granules of the active compound. Hard gelatine capsules may also contain the active compound in combination with a solid powdered carrier such as lactose, saccharose, sorbitol, mannitol, potato starch, corn starch, amylopectin, cellulose derivatives or gelatine.

Dosage units for rectal administration may be prepared in the form of suppositories which contain the active substance mixed with a neutral fat base, or they may be prepared in the form of a gelatine rectal capsule which contains the active substance in a mixture with a vegetable oil, paraffin oil or other suitable vehicle for gelatine rectal capsules, or they may be prepared in the form of a ready-made micro enema, or they may be prepared in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugaralcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior use.

Solutions for parenteral administration may be prepared as a solution of a compound of the invention in a pharmaceutically acceptable solyen, preferably in a concentration from 0.1% to 10% by weight. These solutions may also contain stabilizing unit dose ampoules or vials. Solutions for parenteral administration may also be prepared as a dry preparation to by reconstituted with a suitable solvent extemporaneously before use.

The typical daily dose of the active substance varies within a wide range and will depend on various factors such as for example the individual requirement of each patient, the route of administration and the disease. In general, oral and parenteral dosages will be in the range of 5 to 500 mg per day of active substance.

Pharmaceutical formulations containing a compound of the invention as active ingredient are illustrated in the following examples.

Example A. Syrup.

A syrup containing 1% (weight per volume) of active substance was prepared from the following ingredients:

| | |
|---|---|
| Compound according to Example 49 | 1.0 g |
| Sugar, powder | 30.0 g |
| Saccharine | 0.6 g |
| Glycerol | 5.0 g |
| Flavouring agent | 0.05 g |
| Ethanol 96% | 5.0 g |

| | | |
|---|---|---|
| Distilled water q.s. to a final volume of | | 100 ml |

Sugar and saccharine were dissolved in 60 g of warm water. After cooling the acid addition salt was dissolved in the sugar solution and glycerol and a solution of flavouring agents dissolved in ethanol were added. The mixture was diluted with water to a final volume of 100 ml.

The above given active substance may be replaced with other pharmaceutically acceptable acid addition salts.

Formulation B. Tablets

A tablet containing 50 mg of active compound was prepared from the following ingredients:

| | | |
|---|---|---|
| I | Compound according to Example 49 | 500 g |
| | Lactose | 700 g |
| | Methyl cellulose | 6 g |
| | Polyvinylpyrrolidone cross-linked | 50 g |
| | Magnesium stearate | 15 g |
| | Sodium carbonate | 6 g |
| | Distilled water | q.s. |
| II | Hydroxypropyl methylcellulose | 36 g |
| | Polyethylene glycol | 9 g |
| | Colour Titanium dioxide | 4 g |
| | Purified water | 313 g |

I Compound according to example 49, powder, was mixed with lactose and granulated with a water solution of methyl cellulose and sodium carbonate. The wet mass was forced through a sieve and the granulate dried in an oven. After drying, the granulate was mixed with polyvinylpyrrolidone and magnesium stearate. The dry mixture was pressed into tablet cores (10,000 tablets), each tablet containing 50 mg of acrive substance, in a tabletting machine using 7 mm diameter punches.

II A solution of hydroxypropyl methylcellulose and polyethylene glycol in purified water was prepared. After dispersion of titanium dioxide the solution was sprayed onto the tablets I in an Accela Cora®, Manesty coating equipment. A final tablet weight of 175 mg was obtained.

Formulation C. Solution for intravenous administration

A parenteral formulation for intravenous use, containing 4 mg of active compound per ml, was prepared from the following ingredients:

| | |
|---|---|
| Compound according to Example 49 | 4 g |
| Polyethylene glycol 400 for injection | 400 g |
| Disodium hydrogen phosphate | q.s. |
| Sterile water to a final colume of | 1.000 ml |

Compound according to Example 49 was dissolved in polyethylene glycol 400 and 550 ml of water was added. pH of the solution was brought to pH 7.4 by adding a water solution of disodium hydrogen phosphate and water was added to a final volume of 1000 ml. The solution was filtered through a 0.22 μm filter and immediately despensed into 10 ml sterile ampoules. The ampoules were sealed.

Biological tests

A. Inhibiting effect in vitro on acid secretion in isolated rabbit gastric glands was measured as described by Berglindh et al. (1976), Acta physiol. scand., 97, 401–414.

Most of the compounds in Table 1 had an $IC_{50}$ value in the range of 0,2–100 μM.

B. Inhibiting effect in vivo on acid secretion in conscious female rat was measured according to the following method:

Female rats of the Sprague-Dawley strain were used. They were equipped with cannulated fistulae in the stomach (lumen) and the upper part of the duodenum, for collection of gastric secretions and administration of test substances, respectively. A fourteen days recovery period after surgery was allowed before testing commenced.

Before secretory tests, the animals were deprived of food but not water for 20 h. The stomach was repeatedly washed through the gastric cannula with tapwater (37° C.), and 6 ml of Ringer-Glucose given s.c. Acid secretion was stimulated with infusion during 3.0 h (1,2 ml/h, s.c.) of pentagastrin and carbachol (20 and 110 nmol/kg h, respectively), during which time gastric secretions were collected in 30-min fractions. Test substances or vehicle were given iv or id at 60 min after starting the stimulation, in a volume of 1 ml/kg. Gastric juice samples were titrated to pH 7.0 with NaOH, 0.1 mol/L, and acid output calculated as the product of titrant volume and concentration. Further calculations were based on group mean responses from 4–5 rats. The acid output during the periods after administration of test substances or vehicle were expressed as fractional responses, setting the acid output in the 30-min period preceding administration to 1.0. Percentage inhibition was calculated from the fractional responses elicited by test compound and vehicle. $ED_{50}$-values were obtained from graphical interpolation on log dose-response curves, or estimated from single-dose experiments assuming a similar slope for all dose-response curves. The results are based on gastric acid secretion during two hours after drug/vehicle administration.

The compound according to Example 49 had after id administration an $ED_{50}$ value of 2 μmol/kg.

The compound according to Example 63 had after iv administration an $ED_{50}$ value of 1.3 μmol/kg.

What we claim is:

1. A compound of the formula I

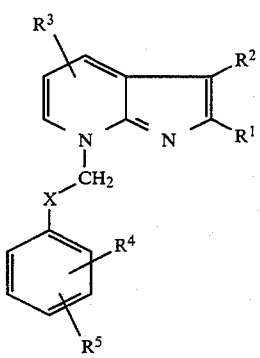

or a pharmaceutically acceptable salt thereof, wherein X represents

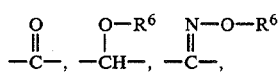

or —CH$_2$—;

R$^1$ represents H, lower alkyl, CH$_2$—O—R$^{7'}$ halogen, phenyl or phenyl substituted with (1-6c) alkyl, (1-6c) alkoxy, (1-6c) acyl, halogen, CF$_3$, CN, NH$_2$, NO$_2$, or (1-6c) alkoxycarbonyl;

R$^2$ represents H, lower alkyl, CH$_2$CN,

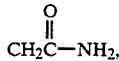

halogen, O—R$^8$,

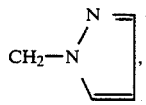

S—CN, CH$_2$OH, CH$_2$C≡CH, CF$_3$,CH$_2$NC or NH$_2$;

R$^3$ represents H, lower alkyl, CF$_3$, O—R$^9$, NH$_2$, lower alkylamino, di-lower alkylamino, halogen, CN,

S—R$^{10}$, or NHCOR$^{10}$;

R$^4$ and R$^5$, which are the same or different, represent H, lower alkyl, CN, halogen, O—R$^{11}$, NO$_2$, NH$_2$, lower alkylamino, di-lower alkylamino, S—R$^{12}$, NHCOR$^{13}$,

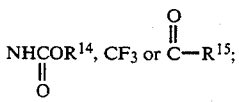

R$^6$, R$^7$, R$^8$, R$^9$, R$^{11}$ and R$^{13}$ which are the same or different, represent H or lower alkyl;

R$^{10}$ represents lower alkyl or phenyl lower alkyl;

R$^{12}$ and R$^{14}$ which are the same or different represent lower alkyl;

R$^{15}$ represents H, lower alkyl, OH or lower alkoxy; provided that R$^1$ and R$^2$ are not simultaneously H.

2. A compound according to claim 1 wherein X is —CO—,

or —CH$_2$— and R$^6$ is H or (1-6C) alkyl.

3. A compound according to claim 1 wherein R$^1$ is (1-6C) alkyl, optionally substituted phenyl, —CH$_2$OR$^7$, or halogen, wherein is H or (1-6C) alkyl.

4. A compound according to claim 1 wherein R$^2$ is H, (1-6C) alkyl, —CH$_2$C≡CH, —CH$_2$OH, —CH$_2$CN, —CH$_2$CONH$_2$, —CH$_2$NC, —NH$_2$,

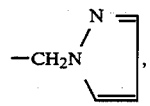

—SCN, halogen, or —CF$_3$.

5. A compound according to claim 1 wherein R$^3$ is H, (1-6C) alkyl, —OR$^9$, —NH$_2$, (1-6C)alkyl-amino (1-6C-)dialkylamino, —CN, —SR$^{10}$, halogen —CF$_3$, or —NHCOR$^{10}$, wherein R$^9$ is H or (1-6C)alkyl, and R$^{10}$ is (1-6C)alkyl or phenyl-(1-6C)-alkyl.

6. A compound according to claim 1 wherein R$^4$ and R$^5$ are the same or different and selected from H, (1-6-C)alkyl, —CN, halogen, —OR$^{11}$, —NO$_2$, —NH$_2$, (1-6C)alkylamino, (1-6C)dialkylamino, —SR$^{12}$, —NHCOR$^{13}$, —CF$_3$, or —COR$^{15}$, wherein R$^{11}$ is H or (1-6-C)alkyl, R$^{12}$ is (1-6C)alkyl, R$^{13}$ is H or (1-6C) alkyl and R$^{15}$ is H, (1-6C)alkyl, OH, or (1-6C) alkoxy.

7. A compound according to claim 1 wherein X is —CO—, —CH, or —CH$_2$—;

R$^1$, is (1-6C)alkyl, optionally substituted phenyl, —CH$_2$OR$^7$, or halogen, and R$^7$ is H or (1-6C)alkyl;

R$^2$ is H, (1-6C)alkyl, —CH$_2$C≡CH, —CH$_2$OH, —CH$_2$CN, —CH$_2$CONH$_2$, —CH$_2$NC, —NH$_2$,

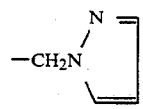

—SCN, halogen, or —CF$_3$;

R$^3$ is H, (1-6)alkyl, —OR$^9$, —NH$_2$, (1-6C)alkylamino, (1-6C)dialkylamino, —CN —SR$^{10}$, halogen, —CF$_3$, or —NHCOR$^{10}$, and R$^9$ is H: or (1-6C)alkyl, and R$^{10}$ is (1-6C)alkyl, or phenyl-(1-6C)-alkyl; and R$^4$ and R$^5$ are the same or different and selected from H, (1-6C)alkyl, —CN, halogen, —OR$^{11}$, —NO$_2$, —NH$_2$, (1-6C)alkylamino, (1-6C)dialkylamino, —SR$^{12}$, —NHCOR$^{13}$, —CF$_3$, or —COR$^{15}$, wherein R$^{11}$ is H or (1-6C)alkyl, R$^{12}$ is (1-6C)alkyl, R$^{13}$ is H or (1-6C)alkyl, and R$^{15}$ is H, (1-6C)alkyl, OH, or (1-6C)alkoxy.

8. A compound according to claim 1 wherein X is —CO—, —CH(OH)—, —CH(OCH$_3$)—, —CH(OC$_2$H$_5$)—, or —CH$_2$—.

9. A compound according to claim 1 wherein R$^1$ is CH$_3$, C$_2$H$_5$, CH(CH$_3$)$_2$, (CH$_2$)$_2$CH$_3$, Cl, Br, or phenyl.

10. A compound according to claim 1 wherein R$^2$ is H, CH$_3$, C$_2$H$_5$, CH$_2$CN, CH$_2$CONH$_2$, F, Cl, Br, —SCN, CH$_2$OH, CH$_2$C≡CH, CF$_3$ or CH$_2$NC.

11. A compound according to claim 1 wherein R$^3$ is H, CH$_3$, C$_2$H$_5$, CH(CH$_3$)$_2$,(CH$_2$)$_2$CH$_3$,CF$_3$, OH, OCH$_3$, OC$_2$H$_5$, OCH(CH$_3$)$_2$, NH$_2$, NHCH$_3$, NHC$_2$H$_5$, N(CH$_3$)$_2$, N(C$_2$H$_5$)$_2$, F, Cl, Br, SCH$_3$, SC$_2$H$_5$,

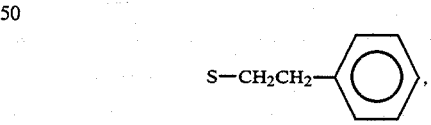

or NHCOCH$_3$.

12. A compound according to claim 1 wherein R$^4$ and R$^5$ which are the same or different, are selected from H, CH$_3$, C$_2$H$_5$, CH(CH$_3$)$_2$, F, Cl, Br, OH, OCH$_3$, OC$_2$H$_5$, OCH(CH$_3$)$_2$, NO$_2$, NH$_2$, NHCH$_3$, NHC$_2$H$_5$, N(CH$_3$)$_2$, N(C$_2$H$_5$)$_2$, SCH$_3$, or CF$_3$.

13. A compound according to claim 1 wherein X is —CO—, —CH(OH)—, CH(OCH$_3$)—, —CH(OC$_2$H$_5$)—, or —CH$_2$—;

R$^1$ is CH$_3$, C$_2$H$_5$,CH(CH$_3$)$_2$, (CH$_2$)$_2$CH$_3$, Cl, Br, or phenyl;

R$^2$ is H, CH$_3$, C$_2$H$_5$, CH$_2$CN, CH$_2$CONH$_2$, F, Cl, Br, —SCN,CH$_2$OH,CH$_2$C≡CH,CF$_3$, or CH$_2$NC;

$R^3$ is H, $CH_3$, $C_2H_5$, $CH(CH_3)_2$, $(CH_2)_2CH_3$, $CF_3$, OH, $OCH_3$, $OC_2H_5$, $OCH(CH_3)_2$, $NH_2$, $NHCH_3$, $NHC_2H_5$, $N(CH_3)_2$, $N(C_2H_5)_2$, F, Cl, Br, $SCH_3$, $SC_2H_5$,

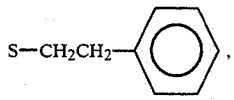

or $NHCOCH_3$;

and $R^4$ and $R^5$ are the same or different and selected from H, $CH_3$, $C_2H_5$, $CH(CH_3,)_2$, F, Cl, Br, OH, $OCH_3$, $OC_2H_5$, $OCH(CH_3)_2$, $NO_2$, $NH_2$, $NHCH_3$, $NHC_2H_5$, $N(CH_3)_2$, $N(C_2H_5)_2$, $SCH_3$, or $CF_3$.

14. A compound according to claim 1 of the formula

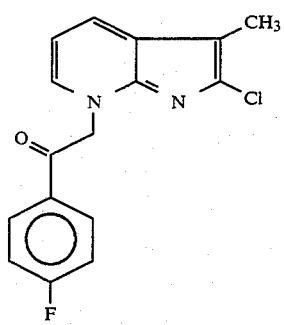

and pharmaceutically acceptable salts thereof.

15. A compound according to claim 1 of the formula

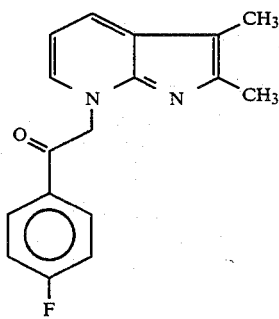

and pharmaceutically acceptable salts thereof.

16. A compound according to claim 1 of the formula

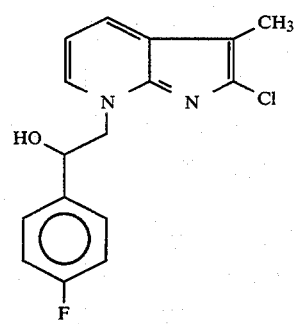

and pharmaceuticallly acceptable salts thereof.

17. A compound according to claim 1 of the formula

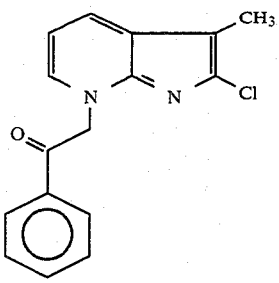

and pharmaceutically acceptable salts thereof.

18. A compound according to claim 1 of the formula

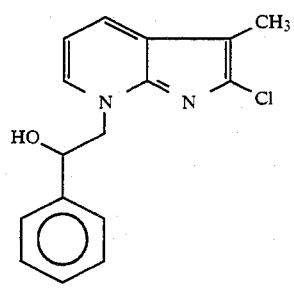

and pharmaceutically acceptable salts thereof.

19. A compound according to claim 1 of the formula

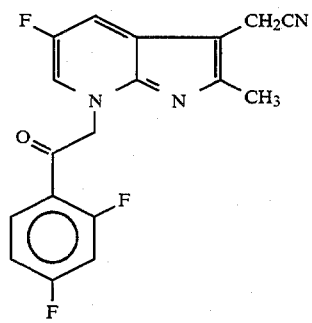

and pharmaceutically acceptable salts thereof.

20. A compound according to claim 1 of the formula

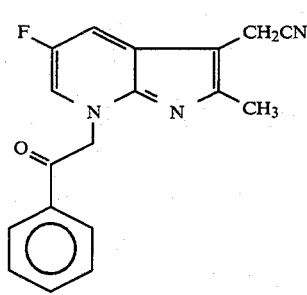

and pharmaceutically acceptable salts thereof.

21. A compound according to claim 1 of the formula

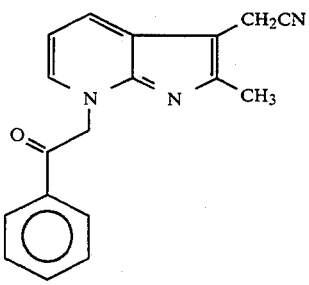

and pharmaceutically acceptable salts thereof.

22. A compound according to claim 1 of the formula

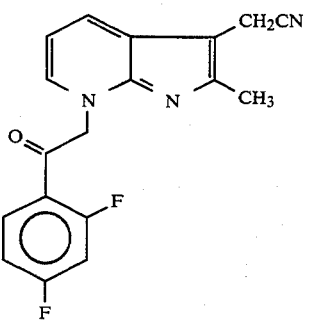

and pharmaceutically acceptable salts thereof.

23. A compound according to claim 1 of the formula

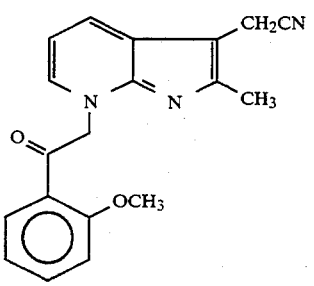

and pharmaceutically acceptable salts thereof.

24. A compound according to claim 1 of the formula

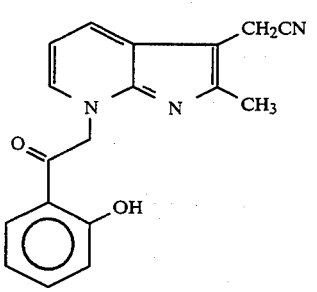

and pharmaceutically acceptable salts thereof.

25. A compound according to claim 1 of the formula

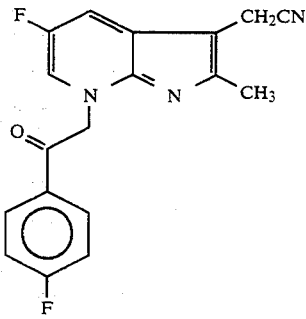

and pharmaceutically acceptable salts thereof.

26. A compound according to claim 1 of the formula

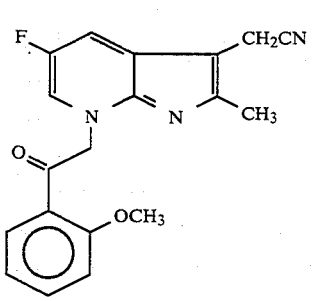

and pharmaceutically acceptable salts thereof.

27. A compound according to claim 1 of the formula

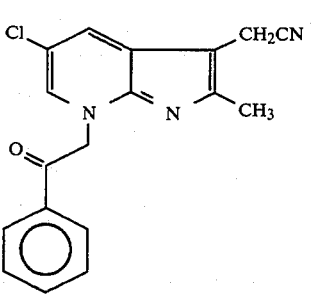

and pharmaceutically acceptable salts thereof.

28. A compound according to claim 1 of the formula and pharmaceutically acceptable salts thereof.

29. A compound according to claim 1 of the formula

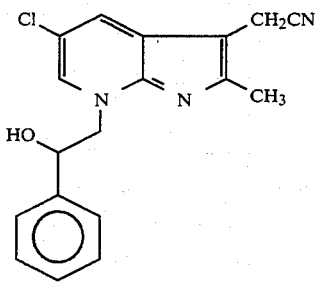

and pharmaceutically acceptable salts thereof.

30. A compound according to claim 1 of the formula

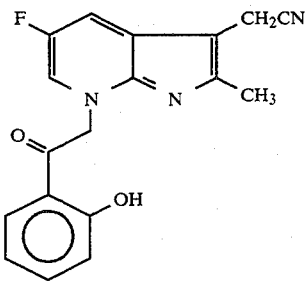

or a pharmaceutically acceptable salt thereof.

31. A pharmaceutical composition containing as active ingredient a compound according to claim 1.

32. A method for inhibiting gastric acid secretion which comprises administering to mammals and man a compound as defined in claim 1.

33. A method for the treatment of gastrointestinal inflammatory diseases in mammals and man which comprises administering a compound as defined in claim 1.

* * * * *